US006783732B2

(12) United States Patent
Madden et al.

(10) Patent No.: US 6,783,732 B2
(45) Date of Patent: Aug. 31, 2004

(54) APPARATUS AND METHOD FOR AVOIDING CROSS-CONTAMINATION DUE TO PENDENT DROPS OF FLUID HANGING FROM DISCHARGE CONDUITS

(75) Inventors: Alfred P Madden, Colorado Springs, CO (US); Jon Hoshizaki, Cupertino, CA (US); Jason H. Halsey, San Francisco, CA (US); Stephen E. Moring, Oskaloosa, KS (US); Mark F. Oldham, Los Gatos, CA (US); Kevin S. Bodner, Belmont, CA (US)

(73) Assignee: Applera Corporation, Foster City, CA (US)

( * ) Notice: Subject to any disclaimer, the term of this patent is extended or adjusted under 35 U.S.C. 154(b) by 43 days.

(21) Appl. No.: 10/199,743

(22) Filed: Jul. 19, 2002

(65) Prior Publication Data

US 2002/0179520 A1 Dec. 5, 2002

Related U.S. Application Data

(62) Division of application No. 09/565,202, filed on May 4, 2000, now Pat. No. 6,506,343, which is a division of application No. 09/182,946, filed on Oct. 29, 1998, now Pat. No. 6,159,368.

(51) Int. Cl.[7] .......................... G01N 35/00; G01N 35/10
(52) U.S. Cl. ......................... 422/63; 422/100
(58) Field of Search ............................. 422/63, 64, 65, 422/100, 101, 103, 104; 435/287.3, 288.3, 288.4, 288.5

(56) References Cited

U.S. PATENT DOCUMENTS 3,463,322 A    8/1969  Gerarde ...................... 210/455

(List continued on next page.)

FOREIGN PATENT DOCUMENTS

DE          40 22 792 A1    2/1992

(List continued on next page.)

OTHER PUBLICATIONS

"GENESIS Robotic Microplate Processor," *TECAN*. Document No. 390981, pp. 1–8. Ver. Nov. 1997.

(List continued on next page.)

*Primary Examiner*—John Kim
(74) *Attorney, Agent, or Firm*—Kilyk & Bowersox, P.L.L.C.

(57) ABSTRACT

The present invention provides multi-well plates and column arrays in which samples (e.g., cell lysates containing nucleic acids of interest, such as RNA) can be analyzed and/or processed. In one embodiment, the microfiltration arrangement is a multilayer structure, including (i) a column plate having an array of minicolumns into which samples can be placed, (ii) a discrete filter element disposed in each minicolumn, (iii) a drip-director plate having a corresponding array of drip directors through which filtrate may egress, and (iv) a receiving-well plate having a corresponding array of receiving wells into which filtrate can flow. The invention provides multi-well microfiltration arrangements that are relatively simple to manufacture and that overcome many of the problems associated with the prior arrangements relating to (i) cross-contamination due to wicking across a common filter sheet or (ii) individual filter elements entrapping sample constituents within substantial dead volumes. Further, the invention provides multi-well microfiltration arrangements that adequately support discrete filter elements disposed in the wells without creating substantial preferential flow. Additionally, the invention provides multi-well microfiltration arrangements that avoid cross-contamination due to aerosol formation, pendent drops and/or splattering. Other disclosed features of the invention provide for the automated covering or heat-sealing of filtrate samples separately collected in an array of wells.

4 Claims, 23 Drawing Sheets

U.S. PATENT DOCUMENTS

| | | | |
|---|---|---|---|
| 3,721,364 A | 3/1973 | Lukaschewitz et al. | 220/41 |
| 4,167,875 A | 9/1979 | Meakin | 73/421 R |
| 4,246,339 A | 1/1981 | Cole et al. | 435/7 |
| 4,279,342 A | 7/1981 | Van Pelt | 206/542 |
| 4,304,865 A | 12/1981 | O'Brien et al. | 435/240 |
| 4,422,151 A | 12/1983 | Gilson | 364/496 |
| 4,734,192 A | 3/1988 | Champion et al. | 210/335 |
| D297,602 S | 9/1988 | Schnur | D7/76 |
| 4,902,481 A | 2/1990 | Clark et al. | 422/101 |
| 4,927,604 A | 5/1990 | Mathus et al. | 422/101 |
| 4,948,442 A | 8/1990 | Manns | 156/73.1 |
| 4,948,564 A | 8/1990 | Root et al. | 422/101 |
| 4,969,306 A | 11/1990 | Wallin | 53/329 |
| 5,002,889 A | 3/1991 | Klein | 435/284 |
| 5,047,215 A | 9/1991 | Manns | 422/101 |
| 5,108,703 A | 4/1992 | Pfost et al. | 422/65 |
| 5,108,704 A | 4/1992 | Bowers et al. | 422/70 |
| 5,110,556 A | 5/1992 | Lyman et al. | 422/101 |
| 5,114,681 A | 5/1992 | Bertoncini et al. | 422/111 |
| 5,116,496 A | 5/1992 | Scott | 210/232 |
| 5,141,719 A | 8/1992 | Fernwood et al. | 422/101 |
| 5,201,348 A | 4/1993 | Lurz | 141/130 |
| 5,208,161 A | 5/1993 | Saunders et al. | 435/286 |
| 5,227,137 A | 7/1993 | Monti et al. | 422/101 |
| 5,264,184 A | 11/1993 | Aysta et al. | 422/101 |
| 5,282,543 A | 2/1994 | Picozza et al. | 220/255 |
| 5,283,039 A | 2/1994 | Aysta | 422/104 |
| 5,326,533 A | 7/1994 | Lee et al. | 422/101 |
| 5,342,581 A | 8/1994 | Sanadi | 422/101 |
| 5,352,086 A | 10/1994 | Mank | 414/797 |
| 5,368,729 A | 11/1994 | Stefkovich et al. | 210/266 |
| 5,380,437 A | 1/1995 | Bertoncini | 210/416.1 |
| 5,384,024 A | 1/1995 | Moring et al. | 204/299 R |
| 5,401,637 A | 3/1995 | Pocock | 435/7.1 |
| 5,409,832 A | 4/1995 | Pocock | 435/287 |
| 5,427,265 A | 6/1995 | Cautereels et al. | 220/318 |
| 5,459,300 A | 10/1995 | Kasman | 219/433 |
| 5,464,541 A | 11/1995 | Aysta et al. | 210/767 |
| 5,475,610 A | 12/1995 | Atwood et al. | 364/500 |
| 5,516,490 A | 5/1996 | Sanadi | 422/101 |
| 5,582,665 A | 12/1996 | Eigen et al. | 156/69 |
| 5,602,756 A | 2/1997 | Atwood et al. | 364/500 |
| 5,604,130 A | 2/1997 | Warner et al. | 435/286.7 |
| 5,620,663 A | 4/1997 | Aysta et al. | 422/104 |
| 5,650,323 A | 7/1997 | Root | 435/284.1 |
| 5,665,247 A | 9/1997 | Valus et al. | 210/767 |
| 5,679,310 A | 10/1997 | Manns | 422/102 |
| 5,681,492 A | 10/1997 | Van Praet | 219/400 |
| 5,710,381 A | 1/1998 | Atwood et al. | 73/864.91 |
| 5,721,136 A | 2/1998 | Finney et al. | 435/287.2 |
| 5,736,105 A | 4/1998 | Astle | 422/100 |
| 5,736,106 A | 4/1998 | Ishiguro et al. | 422/131 |
| 5,741,463 A | 4/1998 | Sanadi | 422/101 |
| 5,792,425 A | 8/1998 | Clark et al. | 422/101 |
| 5,792,430 A | 8/1998 | Hamper | 422/131 |
| 5,846,493 A | 12/1998 | Bankier et al. | 422/101 |
| 6,159,368 A | 12/2000 | Moring et al. | 210/321.75 |
| 6,251,343 B1 | 6/2001 | Dubrow et al. | 422/102 |

FOREIGN PATENT DOCUMENTS

| | | |
|---|---|---|
| DE | 297 22 473 U1 | 4/1998 |
| DE | 196 52 327 A1 | 6/1998 |
| EP | 0 131 934 B1 | 1/1985 |
| EP | 0 359 249 A2 | 3/1990 |
| EP | 0 502 371 B1 | 9/1992 |
| EP | 0 645 187 A2 | 3/1995 |
| EP | 0 676 643 A2 | 10/1995 |
| EP | 0 903 176 A2 | 3/1999 |
| EP | 0 925 828 A1 | 6/1999 |
| GB | 2 246 081 A | 1/1992 |
| WO | WO 86/07606 | 12/1986 |
| WO | WO 94/28111 | 12/1994 |
| WO | WO 95/30139 | 11/1995 |
| WO | WO 98/10853 | 3/1998 |
| WO | WO 00/25922 | 5/2000 |

OTHER PUBLICATIONS

The GENESIS Series of RSPs, *TECAN*. Document No. 390696, pp. 1–8, Ver. Oct. 1997.

"mRNA Isolation Using EVENT," *BIONEWS*. 01:3 (1996).

"Multiscreen® Assay syhstem," *Multiscreen® Assay Systems, Rev. C. Updated: Apr. 13, 1998*. Publication P17479 Revision C. Internet Address: http//millispider.millipore.com/analytical/manuals/p17479a.htm, 1–4.

Newell, J.A. and Horton, H.L. (eds.), "Overload, Tripping, and Stop Mechanisms," *Ingenious Mechanisms*, Industrial Press Inc., New York, 109–111 (1967).

Qiagen Product Guide. 16, 37–38 (1997).

Ruppert, A. et al., *A Filtration Method for Plasmid Isolation Using Microtiter Filter Plates, Analytical Biochemistry*. 230:130–134 (1995).

*Technical Data on Ultra–Pure QM–A Quartz Filters*, Whatman, Data Sheet No. 860 QM–AA (1992).

*Whatman Ultra–Pure QM–A Filters*, Whatman, Data Sheet No. 860 QM–AA (1992).

APPARATUS AND METHOD FOR AVOIDING CROSS-CONTAMINATION DUE TO PENDENT DROPS OF FLUID HANGING FROM DISCHARGE CONDUITS

CROSS-REFERENCE TO RELATED APPLICATIONS

The present application is a divisional of U.S. patent application Ser. No. 09/565,202, filed May 4, 2000, U.S. Pat. No. 6,506,343, which in turn is a divisional of U.S. patent application Ser. No. 09/182,946, filed Oct. 29, 1998 (now U.S. Pat. No. 6,159,368), all of which are hereby incorporated herein in their entireties by reference.

FIELD OF THE INVENTION

The present invention relates to multi-well plates and column arrays in which samples are analyzed or processed.

BACKGROUND OF THE INVENTION

In recent years, microtitration wells have assumed an important role in many biological and biochemical applications, such as sample preparation, genome sequencing, and drug discovery programs. A variety of multi-well arrangements, constructed according to standardized formats, are now popular. For example, a tray or plate having ninety-six depressions or cylindrical wells arranged in a 12×8 regular rectangular array is one particularly popular arrangement.

In some multi-well constructions, a filter sheet or membrane is held against the lower ends, or lips, of open-bottomed wells. Such plates are often manufactured as a multi-layered structure including a unitary sheet of filter material disposed to cover the bottom apertures of all the wells, the filtration sheet being sealed to the outer lip of one or more of the well apertures. The use of a single sheet of filter material in such a manner, however, can lead to cross-contamination between adjacent wells due to the ability of liquid to disperse, e.g., by wicking, across the sheet.

In an effort to overcome this problem, it has been proposed to provide each well with its own discrete filter element or disc. According to one such design, a pre-cut filter disc is inserted into an upper, open end of each well and pushed down until it rests at the bottom of the well. An O-ring is then press-fit down into each well until it comes to rest against the top of the filter disc. The O-ring frictionally engages the column inner wall, thereby retaining the filter in place. While avoiding the cross-contamination problems of unitary filter sheets, such a construction is obviously cumbersome to manufacture. Also, the portion of the disk that gets pinched between the O-ring and the floor of the well introduces a significant "dead volume," which can have an adverse impact on sample purification. For example, sample matrix can become entrapped in these areas along a significant portion of the peripheral edge of individual filter discs. When purifying DNA from blood samples, entrapment of small amounts of hemoglobin (heme) on the edges of a cellulose blot membrane will eventually contaminate the final product in the last stages of the purification process. The contaminating heme residue is a strong inhibitor in PCR and sequencing reaction assays of the DNA products.

Another multi-well arrangement, wherein each well has its own discrete filter element, is formed by positioning a single sheet of filter material between an upper plate, having a plurality of mini-columns formed therein, and a lower plate having a plurality of corresponding "drip directors." Upon bringing the plates together and forming an ultrasonic bond therebetween, the filter sheet is die-cut into individual filter discs positioned below respective mini-columns. Although this construction is easier to manufacture than the above arrangement, it suffers similar disadvantages. Specifically, a substantial portion of each filter disc's peripheral edge becomes pinched between the column plate and the drip director plate, resulting in a significant dead volume that can adversely impact sample purification.

There is, thus, a need for a multi-well microfiltration arrangement that is relatively simple to manufacture, and that overcomes the problems associated with the prior arrangements relating to cross-contamination due to wicking across a common filter sheet, or individual filter discs entrapping sample constituents within substantial dead volumes.

Most of the known multi-well filtration plates, and particularly those providing an individual filter disc for each well, lack adequate space below the filter element to permit an evenly distributed flow of fluid across the filter. In many arrangements, a drip director, at the bottom of each well, provides an expansive, flat surface upon which much of the filter element rests. Preferential flow pathways are thereby created, favoring those areas of the filter element that are not in contact with, or in close proximity to, the drip director surface. Such preferential flow can have an adverse impact on the elution of solutes. For example, preferential flow pathways can impede the leaching of retained sample constituents in non-favored regions of the filter element.

On the other hand, a lack of adequate support beneath each filter element can be problematic, as well. The filter media used in multi-well trays are typically quite thin and exhibit relatively poor mechanical properties. In certain stressful situations, e.g., high-pressure or vacuum filtration, such membranes may not maintain their integrity. Filter discs that are supported only about their peripheral edges might sag, particularly along their central regions, and may even pull loose from the structure holding their edges. For example, a filter disc might collapse into the cavity of a drip director. This would affect the porosity of the filter, trapping certain sample constituents in the filter that would otherwise elute. Moreover, if a bypass forms along the edges of the filter, due to the filter disc pulling away from the peripheral supporting structure, an undesirable loss of sample may result.

There is, thus, a need for a multi-well microfiltration arrangement that adequately supports the filter media at each well, without creating substantial preferential flow.

A few of the known multi-well microfiltration arrangements provide a collection plate, for placement beneath a sample-well plate, having a plurality of closed-bottom collection wells corresponding to the sample wells. Generally, the collection of filtrate takes place upon application of a vacuum to pull the mobile phase through each well. With most of these arrangements, attempts to separately collect the filtrate from each sample well have suffered from unreliable results due to cross-contamination between the wells of the collection plate. A principal cause of such cross-contamination relates to the production of aerosols as the filtrate leaves the drip directors. The aerosols can readily disperse and travel to neighboring collection wells. In addition, aerosols may expose technicians to potentially pathogenic microorganisms, and the like, which may be present in the samples.

Cross-contamination due to aerosol formation is exacerbated by the typical flow pattern induced by the vacuum arrangements of such systems. Usually, the sample-well plate is mounted above the collection plate, and the collection plate, in turn, sits in a vacuum chamber. Upon evacuation of the chamber, solution within each well is drawn down through the filter element toward a respective collection well. Generally, the vacuum draws along flow pathways extending from within each mini-column, through a respective drip director, and horizontally across the top of the collection plate until reaching one side of the collection plate whereat the flow pathways turn downward toward an exit port. Except for those drip directors located directly adjacent the side of the chamber having the exit port, substances (e.g., entrained aerosols, gases, etc.) pulled along each vacuum flow pathway from each drip director must pass by neighboring collection wells as they travel across the top of the collection plate. Unfortunately, aerosols from filtrate exiting one drip director can become entrained in the flow across the collection plate and make its way over into neighboring wells.

The potential for cross-contamination is particularly high when the upper sample-well and drip-director plates are removed from the collection plate. Pendent drops of filtrate remaining on the drip directors can inadvertently fall into neighboring wells as the drip directors are moved over the collection plate. With standard multi-well plates, a concerted, manual "touch-off" of all such pendent drops to the inner sides of respective collection wells is difficult, if not impossible, due to the great number of wells. Application of a strong vacuum below the drip directors, in an attempt to pull such pendent drops down and away from the drip directors, can atomize the pendent drops, resulting in the related problem of contamination by aerosol formation, discussed above.

There is, thus, a need for a multi-well microfiltration arrangement that provides for the separate collection of filtrate from each well, while avoiding cross-contamination due to aerosol formation and/or pendent drops.

SUMMARY OF THE INVENTION

One aspect of the present invention provides a microfiltration apparatus for processing a plurality of fluid samples According to one embodiment, the microfiltration apparatus of the invention includes a first plate having a plurality of columns and a second plate having a plurality of discharge conduits. Each of the columns has a first inner bore defining a lumen within the column and an end region for receiving a filter medium within the column. The column end region defines a second inner bore having a diameter greater than that of the first inner bore and a transition region that joins the second inner bore to the first inner bore. A filter medium for filtering sample is positioned within each column end region, adjacent the transition region. Each discharge conduit has an upstanding upper end region aligned with and received within a corresponding column end region so as to form a substantially fluid-tight interface therebetween. The discharge conduit upper end region has a terminal rim region for supporting a circumferential region of the filter medium such that each filter medium is held between a column transition region and the terminal rim region of a corresponding discharge conduit.

In one embodiment, the transition region of each column has an annular tapered portion. The circumference of the annular tapered portion decreases in a substantially constant fashion along a direction from the second inner bore to the first inner bore. In a related embodiment, a line running along the tapered portion, longitudinally with respect to the column, forms an acute angle with a plane perpendicular to a longitudinal axis of the column and intersecting the column through a junction of the transition region with the second inner bore. The acute angle, in one embodiment, is within the range of about 30–70 degrees. Preferably, the acute angle is within the range of about 30–60 degrees. In one particular embodiment, the acute angle is about 45 degrees.

According to one embodiment, the terminal rim region of each discharge conduit contacts no more than about 15%, and preferably less than about 10%, and more preferably less than about 5% of the bottom surface area of a respective filter medium.

One embodiment provides a plurality of fin-like support buttresses in each of the discharge conduits. In this embodiment, each of the support buttresses has an elongated, narrow, uppermost surface that is substantially coplanar with a plane defined by the terminal rim region of a respective discharge conduit. In a related embodiment, the horizontal cross-sectional area of an upper region of each support buttress decreases in a direction extending towards its uppermost surface in a fashion such that the intersection of the uppermost surface with the plane of the terminal rim region is substantially tangential in nature, forming a line.

According to another embodiment, the microfiltration apparatus is provided with a gas-permeable matrix comprised at least in part of a porous hydrophilic polymer material. The matrix is attached to the second plate on a face opposite the first plate. Also in this embodiment, the matrix circumscribes a plurality of the discharge conduits.

A further embodiment provides means for shifting the first and second plates in either of two directions from a reference "home" position along a generally horizontally extending axis, and then returning the plates back to the reference "home" position. The shifting means can include a stepper motor disposed in mechanical communication with the plates such that angular rotation of the stepper motor induces linear motion of the plates.

In accordance with another embodiment, vacuum means are provided for drawing adherent drops of fluid hanging from the discharge conduits in a direction away from the collection wells and up into the discharge conduits.

In another of its aspects, the present invention provides a method for forming a plurality of microfiltration wells. In one embodiment, a sheet of filter medium is positioned between a first plate containing a plurality of columns and a second plate having a plurality of discharge conduits. Each of the columns has a first inner bore defining a lumen within the column and an end region defining a second inner bore having a diameter greater than that of the first inner bore and a transition region that joins the second inner bore to the first inner bore. Each of the discharge conduits has an upstanding upper end region facing the first plate and aligned with a corresponding column end region. The plates are pressed together in a manner effective to punch portions of the filter medium from the sheet to afford a filter medium plug situated within the end region of each column in abutment with the column transition region and a terminal rim region of a corresponding discharge conduit upper end region.

The method of the invention also provides for the compression-fit sealing of each filter element. In one embodiment, compression of each filter element between the column transition region and a terminal rim region of a corresponding discharge conduit upper end region serves to secure and seal the filter element to an inner sidewall of the column.

In another embodiment, the method further includes the step of securing the first plate to the second plate. The securing step can be effected by forming a bond, such as an ultrasonic weld, between an inner sidewall of each second inner bore and an outer circumferential surface of a respective upper end region.

A further aspect of the present invention provides a microfiltration apparatus for processing a plurality of fluid samples.

In one embodiment, the apparatus includes a first plate having a plurality of columns. Each of the columns contains, at one end thereof, a filter element and a fluid discharge conduit beneath the filter element. A second plate is spaced apart from the first plate by a cavity. The second plate has a plurality of receiving or collection wells that are aligned with the columns for receiving sample fluid from the discharge conduits. The second plate is also provided with a plurality of vents adjacent the collection wells. A gas-permeable matrix is positioned in the cavity between the first plate and the second plate so as to fill the space between the confronting surfaces of the two plates. The matrix laterally surrounds the region between at least one discharge conduit and an aligned collection well. The matrix is effective (i) to permit a vacuum drawn from beneath the second plate to extend, via the vents, to a region above the second plate and to the columns, thereby drawing fluid from the columns into the collection wells and (ii) to obstruct movement of aerosols across the top of the second plate, thereby limiting cross-contamination between wells.

According to one embodiment, the matrix is a continuous sheet having a plurality of openings permitting the passage of filtrate from each discharge conduit to a respective collection well. Each one of the discharge conduits can extend at least partially into a respective one of the openings. Further, the matrix can extend over a plurality of the vents. In one embodiment, the matrix is comprised of a porous hydrophilic polymer material, such as ethyl vinyl acetate (EVA) or the like.

In one embodiment, the collection wells are arranged in a rectangular array having at least eight wells (e.g., 8, 12, 24, 48, or 384 wells). In one preferred arrangement, the second plate is provided with at least one vent for every four collection wells, and the vents are arranged such that a vent is located between each collection well and at least one adjacent collection well. For example, a vent may be provided between each collection well and at least one diagonally adjacent collection well of the array.

According to one embodiment, each of the columns has a first inner bore defining a lumen within the column and an end region defining a second inner bore, having a diameter greater than that of the first inner bore, and a transition region that joins the second inner bore to the first inner bore. Each of the discharge conduits has an upstanding upper end region aligned with and received by a corresponding column end region so as to form a substantially fluid-tight interface therebetween. The discharge conduit upper end region has a terminal rim region for supporting a circumferential region of the filter element such that each filter element is held between a column transition region and the terminal rim region of a corresponding discharge conduit.

In another embodiment, means are provided for shifting the first plate in either of two directions from a reference "home" position along a generally horizontally extending axis, and then returning the plate back to the reference "home" position. The shifting means can include a stepper motor disposed in mechanical communication with the plate such that angular rotation of the stepper motor induces linear movement of the plate.

In a further embodiment, vacuum means are provided for drawing adherent drops of fluid hanging from the discharge conduits in a direction away from the collection wells and up into the discharge conduits.

Another aspect of the present invention provides a method for separately collecting filtrate from an array of microfiltration wells in a corresponding array of closed-bottom collection wells held by a collection tray situated below the is microfiltration-well array.

In one embodiment, the method includes the steps of:
(A) placing a fluid sample in a plurality of the microfiltration wells;
(B) drawing a vacuum along pathways extending from each microfiltration well downward through a plane defined by an upper surface of the collection tray at a point at or adjacent a corresponding collection well to a region beneath the collection tray, thereby causing a filtrate to flow from each microfiltration well and to collect in corresponding collection wells, and
(C) obstructing aerosols formed from the filtrate at any one microfiltration well from moving across the upper surface of the collection tray to a non-corresponding collection well, thereby limiting cross-contamination.

According to one embodiment, each vacuum pathway passes through a gas-permeable matrix disposed in a cavity between the microfiltration-well array and the collection-well array. The gas-permeable matrix can be comprised of a porous hydrophilic polymer material, such as ethyl vinyl acetate (EVA) or the like. In one preferred arrangement, the gas-permeable matrix circumscribes the region between each microfiltration well and a corresponding collection well.

In one embodiment, the vacuum pathways pass through the plane of the collection-tray upper surface by way of vents that traverse the collection tray proximate each of said collection wells. Also in this embodiment, the gas-permeable matrix covers the vents.

In another embodiment, each of the vacuum pathways extends from one microfiltration well into a respective collection well prior to passing through the vents.

In a further embodiment, wherein a collection tray having open-bottom wells is used, the vacuum pathways pass through the plane of the collection-tray upper surface and then down and out of the open bottoms of the wells.

The microfiltration wells comprise, according to one embodiment, a first plate having a plurality of columns and a second plate having a plurality of discharge conduits. Each column has a first inner bore defining a lumen within the column and an end region for receiving a filter medium within the column. The end region defines a second inner bore having a diameter greater than that of the first inner bore and a transition region that joins the second inner bore to the first inner bore. A filter medium for filtering sample is positioned within each column end region, adjacent the transition region. Each discharge conduit has an upstanding upper end region aligned with and received within a corresponding column end region so as to form a substantially fluid-tight interface therebetween. The discharge conduit upper end region has a terminal rim region for supporting a circumferential region of the filter medium such that each filter medium is held between a column transition region and the terminal rim region of a corresponding discharge conduit.

In one embodiment, the method includes the additional steps of:

(i) touching-off, in a substantially simultaneous fashion, adherent drops of fluid hanging from the bottom of each microfiltration well to an inner sidewall of a respective collection well; and (ii) drawing adherent drops of fluid hanging from the discharge conduits in a direction away from the corresponding collection wells and up into the discharge conduits.

In another of its aspects, the present invention provides an apparatus for avoiding cross-contamination due to pendent drops of fluid hanging from a plurality of discharge conduits disposed in an array above a corresponding array of collection wells.

According to one embodiment, the apparatus includes:

(i) a carriage configured to carry one of the arrays and adapted for linear reciprocal motion in either of two directions along a first, generally horizontal, axis from a neutral position whereat the arrays are substantially axially aligned;

(ii) a stepper motor;

(iii) a linkage assembly mechanically communicating the stepper motor with the carriage such that each rotational step of the stepper motor induces movement of the carriage a given distance from the neutral position in one of the two directions depending upon the direction of angular rotation of the motor, thereby effecting relative motion between the discharge-conduit array and the collection-well array such that pendent drops of fluid hanging from the discharge conduits are simultaneously touched-off to inner sidewalls of corresponding collection wells; and (iv) a compression spring mounted within the linkage assembly in a manner permitting the spring (a) to provide a predetermined amount of resistance to movement of the carriage from the neutral position, and (b) to compensate or absorb some of the linear overshoot due to excess angular rotation of the motor beyond the amount required to move the discharge conduits into firm abutment with the inner sidewalls of the collection wells.

In one embodiment, a vacuum chamber communicates with the discharge-conduit array from a side thereof opposite the collection-well array. Evacuation of the vacuum chamber is effective to urge pendent drops of fluid hanging from the discharge conduits in a direction away from the collection wells and into the discharge conduits.

In one preferred embodiment, the carriage is configured to carry the discharge-conduit array, while the collection-well array remains stationary. A vertical positioning assembly can be disposed on the carriage to support the discharge-conduit array for linear movement along a second, generally vertical, axis between a lowered position whereat the discharge conduits extend down into respective collection wells and an elevated position whereat the discharge conduits clear the collection wells.

Still a further aspect of the present invention provides a method for avoiding cross-contamination due to pendent drops of fluid hanging from a plurality of discharge conduits disposed in an array above a corresponding array of closed-bottom collection wells.

In one embodiment, the method includes the steps of:

to (i) touching-off, in a substantially simultaneous fashion, pendent drops of fluid hanging from the discharge conduits to inner sidewalls of respective collection wells; and (ii) drawing pendent drops of fluid hanging from the discharge conduits in a direction away from the corresponding collection-well array and into the discharge conduits.

The touching-off step can be carried out by shifting the discharge-conduit array along a plane substantially orthogonal to the longitudinal axes of the collection wells, while the collection wells are maintained in a substantially fixed position. In one embodiment, each of the discharge conduits is shifted into contact with one sidewall portion of a respective collection wed, and then is shifted into contact with another, laterally opposing sidewall portion of the respective collection well.

One embodiment provides a stepper motor in mechanical communication with the discharge-conduit array such that angular rotation of the stepper motor induces linear motion of the discharge conduits. In this embodiment, stepping of the stepper motor causes the discharge-conduit array to shift.

The step of drawing pendent drops of fluid can be effected by establishing a reduced pressure (a vacuum) above the discharge conduits.

In one embodiment, an upstanding upper end region of each of the discharge conduits is received within a respective column, thereby forming an array of microfiltration wells. Each column has a first inner bore defining a lumen within the column and an end region defining a second inner bore having a diameter greater than that of the first inner bore and a transition region that joins the second inner bore to the first inner bore. A filter element is disposed in each column, between the transition region of the column and the upper end region of a respective discharge conduit.

In another of its aspects, the present invention provides a removable cover for isolating a plurality of samples separately contained in an array of closed-bottom wells supported in a collection tray.

According to one embodiment, the cover includes a substantially rigid, rectangular shell portion having a top surface, a bottom surface and a circumferential side-edge region. A plurality of reversibly expandable, tubular sleeves are provided on the top surface of the shell portion. A resiliently compliant undersurface is secured to the bottom surface of the shell portion. A plurality of resiliently deflectable, elongated side arms project below the bottom surface from opposing side-edge regions of the shell portion. In its normal (unstressed) state, each side arm is positioned substantially perpendicular to a plane defined by the bottom surface. An inwardly directed catch is formed at an end of each side arm, distal from the shell portion. The arms, and associated catches, are useful for releasably snap-locking the cover over the wells of a collection tray.

In one embodiment, the undersurface of the cover includes a plurality of downwardly convex nodules (half-dome features) disposed in an array complementary to the collection-well array. Each nodule is adapted to fit over a corresponding well when the cover is secured over the collection tray.

A further aspect of the invention provides a method for covering an array of open-top wells held in a collection tray.

According to one embodiment, the method is carried out in a substantially automated fashion using (i) a support structure adapted for movement along a generally horizontal plane (x/y direction) and (ii) a plurality of elongated, parallel rods depending from the support and adapted for movement along their respective longitudinal axes (y direction). Initially, the rods, while disposed in a retracted position adjacent the support, are positioned over a cover member. Two of the rods are then extended away from the support (y direction) so that their end regions become wedged in respective cavities formed along the top of the cover, while two rods are maintained in the retracted position (i.e., with free end regions). The cover member is then lifted by retracting the wedged rods back toward the support. The support is then moved along the x/y direction so that the cover becomes positioned over the collection tray. The wedged rods are then extended away from the support so that the cover is lowered onto the collection tray, over the well openings. The free ends of two retracted rods are then extended until they abut an upper region of the cover, thereby blocking upward movement of the cover, while the wedged rods are retracted away from the cover so that they are withdrawn (unwedged) from the cavities. As a result, the cover is left resting on top of the collection tray over the well openings.

From this position, the cover member can be releasably snap-locked to the collection tray. This can be effected, for example, by extending at least one of the rods away from the support and into abutment with an upper region of the cover, thereby pressing the cover into locking engagement with the collection tray. Another of the rods can be extended away from the support and into abutment with another upper region of the cover in order to prevent the cover from flipping up while being locked.

The method can be carried out, for example, with a cover having (i) an upper, substantially rigid shell portion, (ii) a lower, compliant undersurface secured to the shell portion, and (iii) means for releasably locking the shell portion to the collection tray. The undersurface of the cover can include, for example, a plurality of downwardly convex nodules (half-dome features), disposed in an array complementary to the well array. Further, the shell portion can include a plurality of landing sites along its upper surface configured to receive the lower end regions of the rods.

Still a further aspect of the invention provides a device for holding a plurality of rectangular, heat-sealable sheets.

In an exemplary embodiment, the device is comprised of a tray having a substantially rectangular bottom surface, four upwardly divergent sidewalls extending from the bottom surface, and an upper circumferential edge region defining a substantially rectangular open top. A plurality of ribs run along each sidewall, spanning most of the distance between the bottom surface and the upper circumferential edge region. Each of the ribs has a substantially linear surface that (i) faces an opposing sidewall and (ii) is substantially normal to a plane defined by the bottom surface of the tray.

According to one embodiment, a plurality of heat-sealable sheets, arranged in a vertical stack, is positioned in the tray such that peripheral side-edge regions of the sheets are disposed in contact with the substantially linear surface of each rib.

Another aspect of the present invention provides a method of sealing a rectangular, heat-sealable sheet over an array of wells held in a collection tray.

In one embodiment, the method includes the steps of (i) picking up a clear heat-sealable sheet; (ii) placing the sheet over open upper ends of the wells; and (iii) pressing a conformable heated surface against the sheet, from a side opposite the collection tray, with sufficient pressure such that the sheet is heat-sealed to the collection tray over the open upper ends of the wells. Further according to this embodiment, the conformable heated surface is pressed against the sheet using a plurality of spaced-apart elongated rods, disposed substantially normal to an upper surface of the collection plate. The rods can depend from a support structure positioned above the collection plate.

These and other features and advantages of the present invention will become clear from the following description.

BRIEF DESCRIPTION OF THE FIGURES

The structure and manner of operation of the invention, together with the further objects and advantages thereof, may best be understood by reference to the following description taken in conjunction with the accompanying drawings, in which identical reference numerals identify similar elements, and in which.

DETAILED DESCRIPTION OF THE INVENTION

The following discussion of the preferred embodiments of the present invention is merely exemplary in nature. Accordingly, this discussion is in no way intended to limit the scope of the invention, application of the invention, or the uses of the invention.

Figure 1:
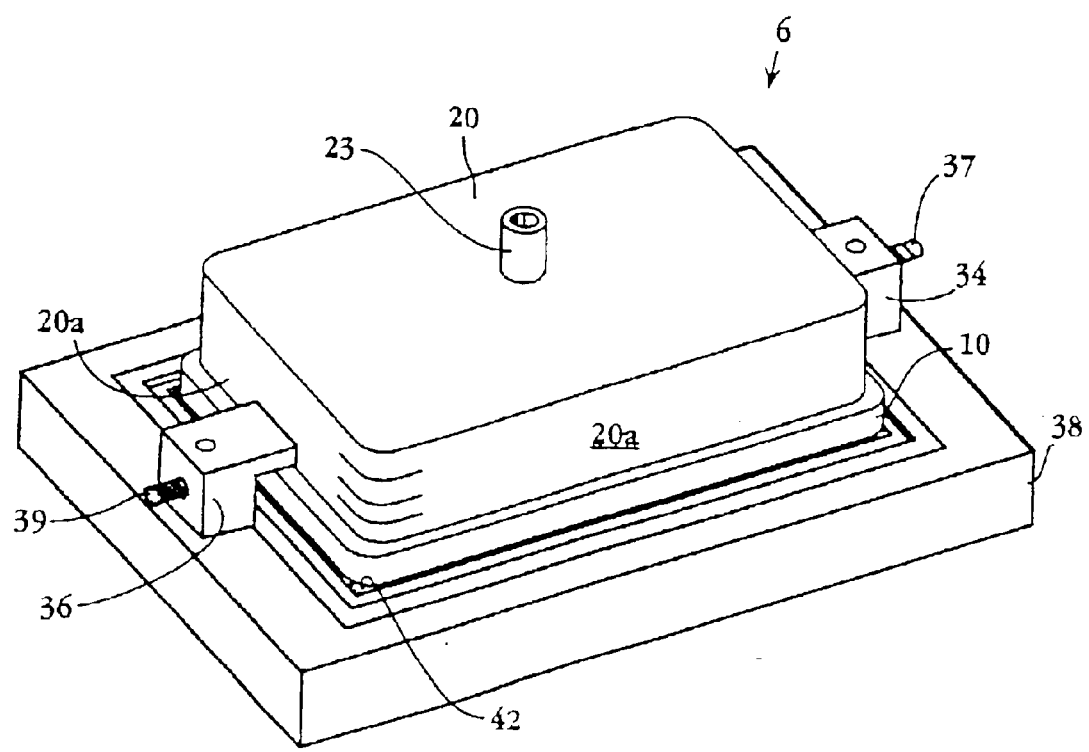
FIG. 1 is a perspective view of a multi-well microfiltration apparatus constructed in accordance with an embodiment of the present invention.
Figure 2:
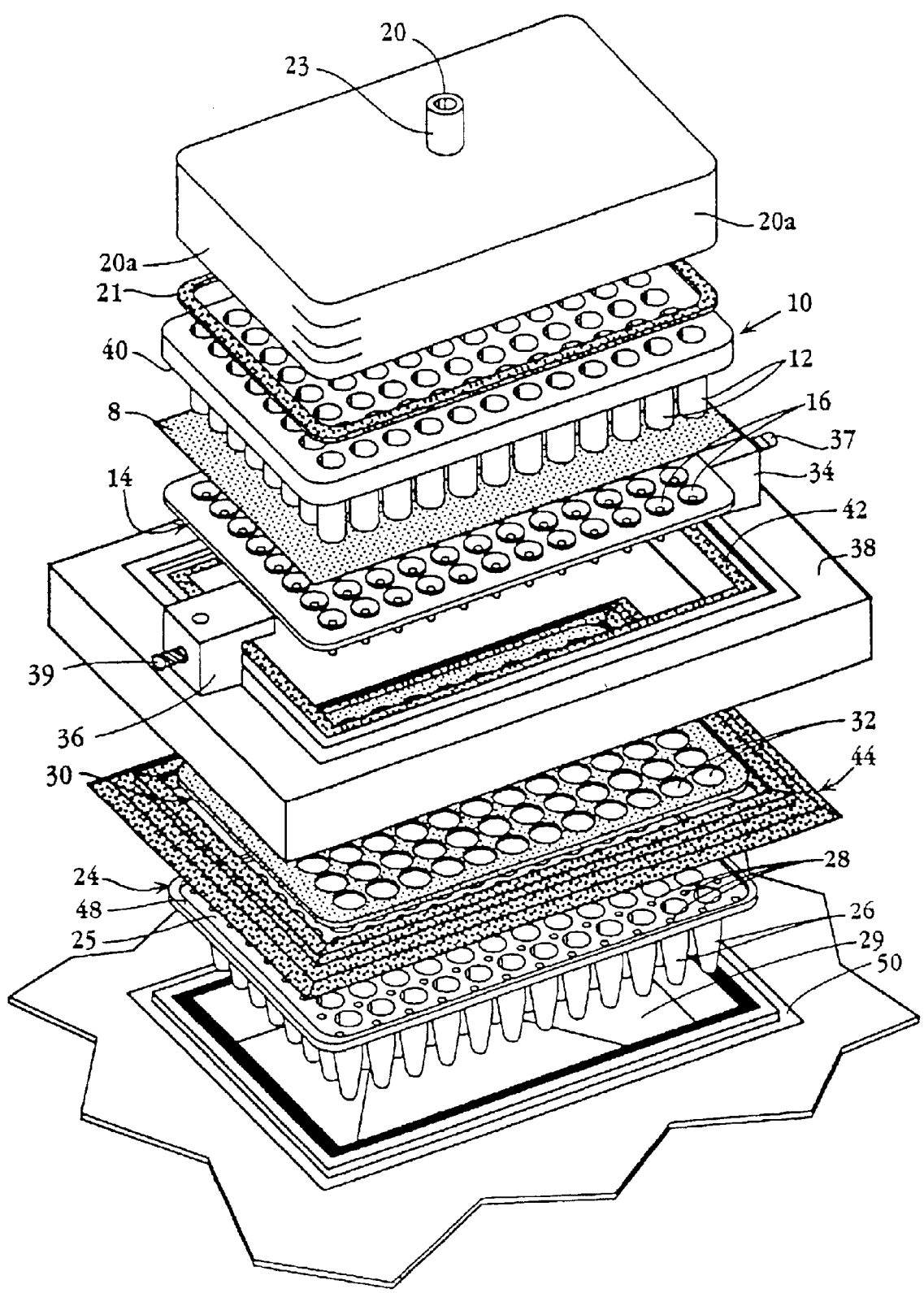
FIG. 2 is an exploded view of the multi-well microfiltration apparatus of FIG. 1.
Figure 3:
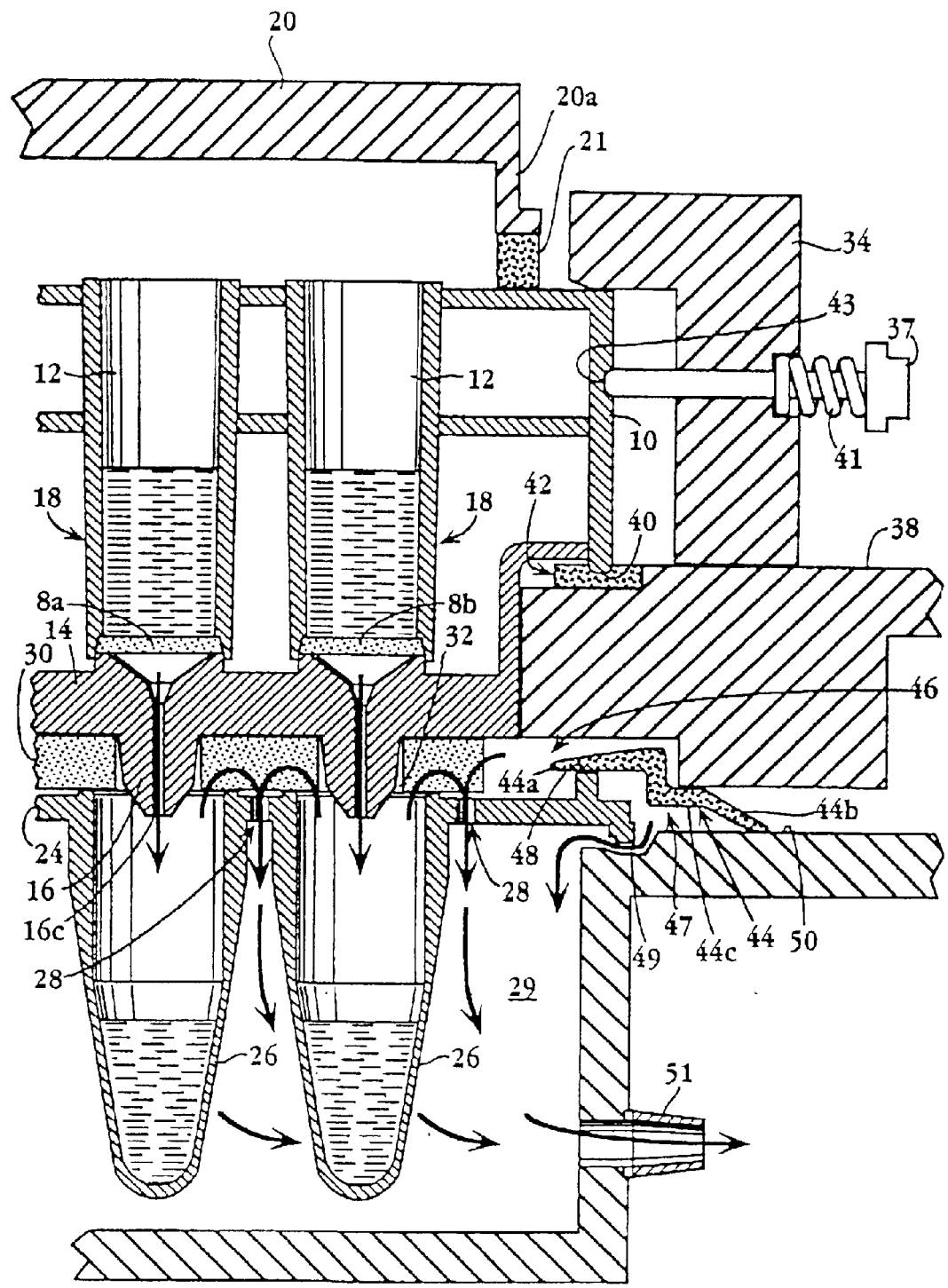
FIG. 3 is a partial side-sectional view of the multi-well microfiltration apparatus of FIGS. 1 and 2.

FIGS. 1–3 show, in perspective, exploded and partial side-sectional views, respectively, an embodiment of a multi-well microfiltration apparatus constructed in accordance with the present invention. In the assembly stage of manufacture, a filter sheet or membrane, indicated in FIG. 2 by the reference numeral 8, is located between a column tray, or plate, 10 having an array of open-bottom minicolumns, such as 12, and a drip-director tray, or plate, 14 having an array of drip directors, such as 16, corresponding to the minicolumns. Upon registering and mating minicolumns 12 with drip directors 16, an array of microfiltration wells are formed, denoted generally in FIG. 3 by the reference numeral 18, each having a discrete filter element or medium (e.g., a plug, disc, or the like), such as 8a and 8b, positioned therein. The inner walls of each mated minicolumn/drip-director pair bound a flow pathway which extends downward through the well 18.

As shown in FIGS. 2 and 3, each microfiltration well has an interior region, or lumen, that is substantially circular in horizontal cross-section. It should be appreciated, however, that microfiltration wells of any desired geometrical cross-section (e.g., oval, square, rectangular, triangular, etc.) could be used. Similarly, the wells may be of any desired shape when viewed along their longitudinal axes, e.g., straight, tapered or other shape. In one embodiment, the walls of each well have a slight outward taper (i.e., the well diameter increases) along the direction extending from the well's upper, loading end toward the filter medium.

The plates of the microfiltration apparatus may be constructed of any substantially rigid, water-insoluble, fluid-impervious material that is substantially chemically non-reactive with the assay samples. The term "substantially rigid" as used herein is intended to mean that the material will resist deformation or warping under a light mechanical or thermal load, although the material may be somewhat elastic. Suitable materials include acrylics, polycarbonates, polypropylenes and polysulfones. Also, it should be noted that the terms "tray" and "plate" are used synonymously and interchangably herein.

Optionally, the fluid-contacting surfaces of the drip directors can be comprised of a material and/or provided with a coating that renders such surfaces hydrophobic, reducing the potential for cross-contamination. For example, low surface-energy materials could be used in forming and/or coating the drip directors. Of course, such materials should be compatible with the assay samples.

The plates may be formed by any conventional means, injection molding being a particularly convenient technique. One embodiment of the invention contemplates the use of injection molded rectangular plastic plates, the length and width of which conform to the commonly used standard of 5.03"×3.37" (127.8 mm and 85.5 mm). In the embodiment of FIGS. 1–3, the wells are formed integrally with such a plate, arranged in a 12×8 regular rectangular array spaced 0.9 cm center-to-center. Alternatively, the wells can be formed as discrete units (not shown) interconnected by plastic webbing to provide an array. In another embodiment, the wells are provided in the form of strips (not shown). For example, a plurality of wells could be disposed in a row with adjacent wells connected to one another by any suitable means, e.g., frangible plastic webs. A plurality of strips could then be arranged side-by-side within a frame designed to hold such strips. For example, twelve 8-well strips could be placed side-by-side in a rectangular frame to form a 96-well array. In a further embodiment, each well is formed as a discrete unit removably positioned within a respective opening formed in a support plate (not shown). For example, a tray could be provided with a 12×8 array of circular openings in which cylindrical wells are received and held, in a fashion similar to test-tubes held in a conventional test-tube rack.

Although the illustrated embodiments show arrangements configured in accordance with the popular 96-well format, the invention also contemplates any other reasonable number of wells (e.g., 12, 24, 48, 384, etc.) disposed in any suitable configuration.

With reference once again to FIGS. 1–3, an upper vacuum chamber 20 is situated above column plate 10. Upper vacuum chamber 20 is adapted for movement between (i) a mounted position, whereat four depending circumferential walls, denoted as 20a, form a substantially airtight seal with an upper, peripheral surface of column plate 10 via an interposed resilient gasket 21, and (ii) a retracted position, whereat chamber 20 is spaced apart from column plate 10. The hollow interior of chamber 20 is pneumatically connectable to an external vacuum source via a hosecock 23 extending through the top of chamber 23. A reduced pressure can be established above the sample wells by bringing chamber 20 to its mounted position atop column plate 10 and then evacuating chamber 20.

In some situations, it may be desirable to establish an increased pressure above the sample wells (e.g., to facilitate the flow of samples through the filter media and out of the wells via the lower discharge conduits). In such cases, chamber 20 can be pressurized by way of a suitable pressure source (e.g., a pump).

A receiving, or collection, plate 24 is located below drip director plate 14. Collection plate 24 includes an upper planar surface, denoted as 25, and an array of closed-bottom wells, such as 26, depending therefrom. The collection-well array corresponds to the drip-director array, permitting the separate collection of filtrate from each sample well. The collection plate is adapted to fit inside an open reservoir of a lower vacuum chamber, denoted as 29, with the collection wells extending down into the reservoir.

Apertures or vents, such as 28, extend through the upper planar surface 25 of collection plate 24. For reasons that will become apparent, at least one aperture should be located adjacent each collection well. The apertures 28 permit fluid communication between the regions above and below the plate 24. By this construction, a vacuum drawn from beneath the collection plate will extend to the regions above the plate and inside the wells.

Although not shown in the figures, the present invention also provides a plate like collection plate 24, except having open-bottom wells as opposed to the closed-bottom wells of plate 24. Otherwise, the plate of open-bottom wells is configured like collection plate 24. That is, the plate of open-bottom wells provides structure for effectively carrying out filtrations and/or washings, while avoiding cross-contamination. However, instead of separately collecting filtrate in the various wells, the filtrate passes through the wells and out of the open bottoms. It is contemplated that the plate of open-bottom wells will be used in a manner like that described herein for plate 24, except that the situation will not call for the separate collection of filtrate. For example, the plate of open-bottom wells is particularly useful in performing intermediate washings. As used herein, "collection plate" and "receiving plate" are used synonymously and interchangably, with either term referring to a plate, intended for placement beneath a drip-director array, having either open-bottom wells or closed-bottom wells, as appropriate for the task at hand. Where the separate collection of filtrate is to take place, it is understood that the wells are of a closed-bottom type. Optionally, a collection plate having open-bottom wells may be formed without vent features (such as 28), as the vacuum can flow directly down and out through the bottom of each well.

A cross-flow restrictor (also referred to as an aerosol guard), denoted as 30, which is generally pervious to gases but substantially impervious to aerosols, is interposed between the upper surface of collection plate 24 and the lower surface of drip-director plate 14. In the illustrated embodiment, cross-flow restrictor 30 has a plurality of passages, such as 32, arranged in an array complementing the collection-well and drip-director arrays. Passages 32 permit filtrate to pass from each drip director 16 to a corresponding collection well 26. In the illustrated arrangement, each drip director 16 extends through a respective passage. Except for such passages, cross-flow restrictor 30 substantially fills the area between the confronting faces of the drip-director and collection-well plates (14, 24).

Preferably, means are provided for supporting the assembled mini-column and drip-director plate arrangement, and assisting in the formation of an airtight seal between this arrangement and the lower vacuum chamber 29. In the illustrated embodiment, a rectangular carriage frame, denoted as 38, is configured to support the mini-column and drip-director plate assembly. Clamps 34, 36 are pivotally mounted about generally vertically extending axes at opposing ends of frame 38. Clamps 34, 36 are operable to engage and hold the column and drip-director assembly on frame 38, with a lower peripheral edge 40 of the column and drip-director plate assembly pressed against a gasket 42 disposed on the upper surface of frame 38 about the frame's central opening.

A spring-loaded centering pin, such as 37 and 39, may extend through each clamp 34, 36. In the embodiment of FIG. 3, centering pin 37 has a shank that is urged by a spring 41 to sit within a complementary recess or depression 43 formed in a sidewall of column plate 10. In another embodiment (not shown), three spring-loaded centering pins are employed, with two pins located at positions on a long side of the arrangement and one pin located at a position on a short side, together operable to push the tray against a corner. In this way, the components can be readily centered (on axis).

A stepped gasket, indicated generally at 44, is disposed adjacent a lower surface of frame 38 about the frame's central opening. Gasket 44 has (i) an upper, inwardly projecting flap portion, denoted as 44a, having a lower surface adapted to engage an upwardly projecting ridge 48 disposed about the periphery of collection plate 24, and (ii) a lower flap portion, denoted as 44b, that extends diagonally downward and outward for engaging an upper surface 50 surrounding the open reservoir of lower vacuum chamber 29. A central plateau region of stepped gasket 44, denoted as 44c, is secured to frame 38 by any suitable means. For example, central plateau region 44c can be attached using an adhesive and/or fasteners. In one embodiment, gasket 44 is interposed between frame 38 and a rectangular clamping frame (not shown). In this embodiment, the rectangular clamping frame is disposed adjacent the plateau region 44c of gasket 44, on a side of gasket 44 opposite frame 38. The clamping frame is then snugly secured to frame 38 using threaded fasteners that pass through aligned passages (not shown) formed in the clamping frame and gasket, and are received in internally threaded bores extending partially into frame 38 from the frame's lower surface. Together, upper gasket 42 and lower gasket 44 assist in forming substantially airtight seals between (i) the upper microfiltration well assembly and the carriage frame, and (ii) the carnage frame and the lower vacuum chamber assembly, respectively.

The gaskets (21, 42, and 44) may be formed of any deformable, resilient, substantially inert material capable of forming a seal. Examples of such materials are silicone, rubber, polyurethane elastomer and polyvinyl chloride. The thickness of each gasket is not critical, provided only that it is sufficient to form a seal. Typical gasket thicknesses will range from about 1 mm to about 5 mm.

Once appropriate airtight seals are formed, evacuation of lower vacuum chamber 29 establishes a substantially uniform pressure drop over all of the sample wells 18, permitting a plurality of individual samples (e.g., up to ninety-six in the illustrated embodiment) to be processed simultaneously on the membrane of choice.

Those skilled in the art will recognize that the choice of filter medium will depend on the intended use of the well. For example, the filter medium might serve as a size exclusion filter, or it could serve as a solid phase interacting with a species in the liquid phase to immobilize such species upon contact, such as an immunological interaction or any other type of affinity interaction. Examples of suitable filters include, but are not limited to, those of nitrocellulose, regenerated cellulose, nylon, polysulfone, glass fiber, blown microfibers, and paper. Suitable filters are available from a variety of sources, e.g., Schleicher & Schuell, Inc. (Keene, N.H.) and Millipore Corp. (Bedford, Mass).

Additional examples of suitable filters include microfiber filters of ultra-pure quartz ($SiO_2$), e.g., as manufactured by Whatman, Inc. (Tewksbury, Mass.) and sold under the trademarks QM-A and QM-B. QM-A filters are about 0.45 mm thick and retain particles of about 0.6 μm. QM-B filters are of the same composition as QM-A, but are two times thicker and therefore provide a longer tortuous path to flow. In one embodiment, a quartz or glass filter element is fired (e.g., at about 400° C.) prior to placement in a microfiltration well in order to reduce particle generation, thereby reducing the potential for clogging of the drip directors.

In another embodiment the filter medium is a porous element that acts as a frit, serving to contain a column packing material (e.g., reversed-phase or size-exclusion packings).

Certain aspects of the invention that address the aforementioned problems pertaining to (i) cross-contamination due to wicking across a common filter sheet and (ii) individual filter elements entrapping sample constituents within substantial dead volumes will now be described in greater detail.

Figure 4:
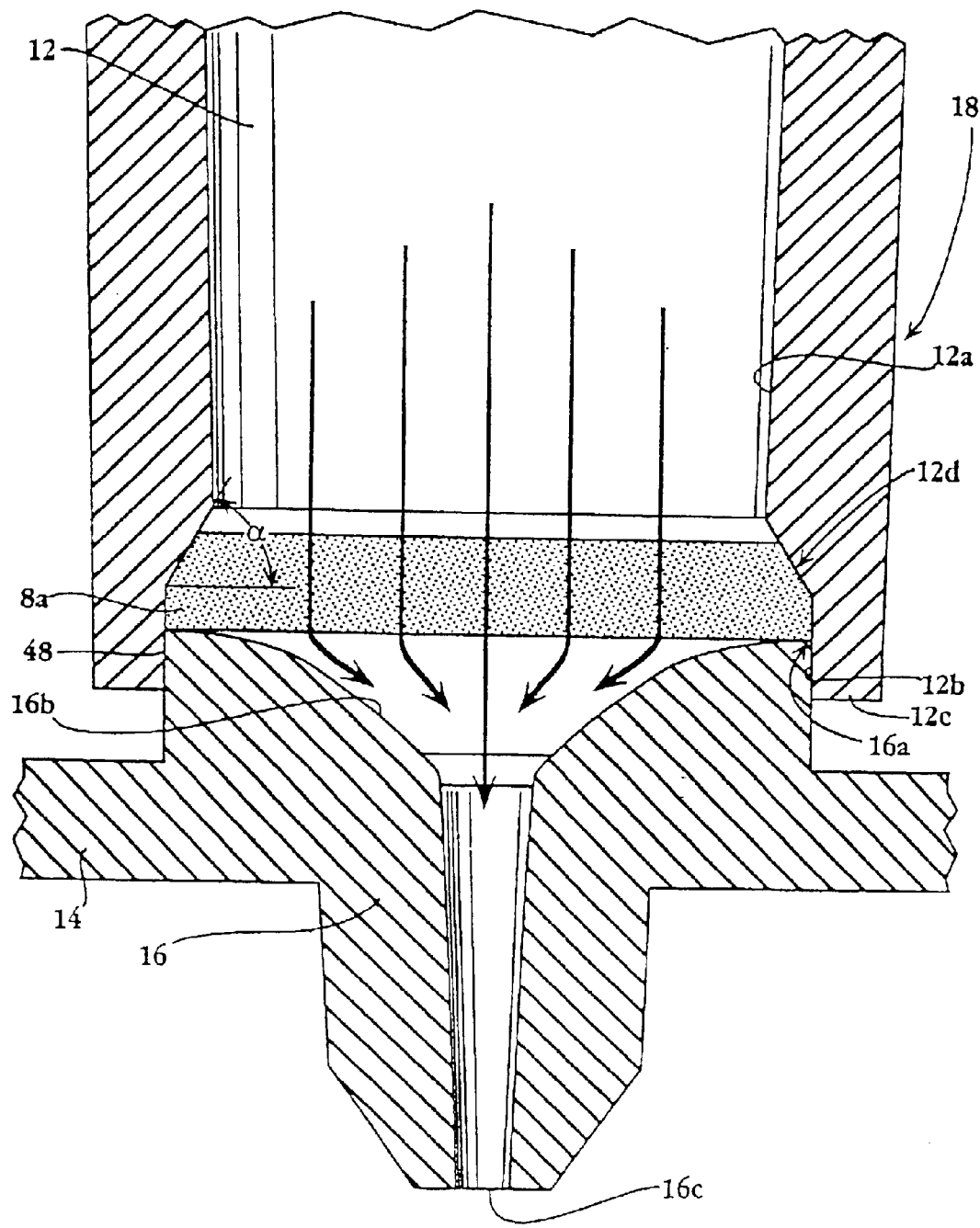
FIG. 4 shows, in enlarged detail, one microfiltration well from the sectional view of FIG. 3.

One microfiltration well from the sectional view of FIG. 3 is shown in enlarged detail in FIG. 4. Mini-column 12 and drip director 16 are axially aligned and mated, with an upwardly protruding portion of drip director 16 snugly received within the lower region of the mini-column lumen to form a substantially fluid-tight well 18.

Means are provided for holding the drip director and mini-column together. In one embodiment, ultrasonic welds or bonds (not shown) formed along an annular region of contact, as designated in FIG. 4 by the reference numeral 48, hold mini-column 12 and drip director 16 together. It should be appreciated that such a weld or bond helps to ensure a fluid-tight interface between these elements. In another embodiment, the mini-column 12 and drip director 16 are held together by a tongue-in-groove arrangement (not shown) formed along confronting surfaces of plates 10 and 14. For example, the column plate could be formed with deep scoring or grooves along its lower surface, circumscribing each well. The upper surface of the drip-director plate could be provided with upwardly projecting ridges, disposed in a pattern complementary to the groove pattern of the column plate and configured to snap-fit within the grooves. Alternatively, the mating of the drip directors with the mini-columns may be sufficiently snug as to hold the plates together solely by frictional engagement.

Means are provided for holding each individual filter element within a respective assembled microfiltration well. In this regard, each filter element is disposed within the mini-column lumen so that a portion of its peripheral edge is held between (i) a constricted-diameter region within the lower portion of the mini-column and (ii) an upper portion of the drip director. The central region of the filter element extends fully across the mini-column lumen.

In the embodiment of FIG. 4, mini-column 12 is formed with a bore 12a and a counterbore 12b, the latter extending upwardly from the mini-column's lower end or lip 12c. Between the bore 12a and counterbore 12b, lies a transition region. The transition region provides a constricted-diameter region, or shoulder, within the mini-column lumen capable of cooperating with an upper portion of a corresponding drip director to maintain the filter element in place. The junctions of the transition region with the bore and counterbore may be of any suitable shape. For example, such junctions could take the shape of a hard angle or corner, or alternatively, they could take the shape of a smooth curve. Further, the transition region itself, between such junctions, may be of any shape, e.g., flat, curved, stepped, or any combination thereof, provided only that a suitable constricted-diameter region is provided in the mini-column lumen for contacting an upper edge region of the filter element.

In one preferred embodiment, depicted in FIG. 4, the transition region between bore 12a and counterbore 12b defines an internal, annular shoulder, denoted as 12d. In this embodiment, each of the junctions of shoulder 12d with bore 12a and counterbore 12b defines a hard angle or corner. Between such junctions, the shoulder 12d takes the form of an annular wall having a substantially constant taper, with a decreasing circumference along the direction from counterbore 12b to bore 12a. Longitudinally, the surface of shoulder 12d is oblique to the surfaces of bore 12a and counterbore 12b. Preferably, the surface of shoulder 12d forms an acute angle with a plane perpendicular to the mini-column's central axis and extending through the junction of shoulder 12d with counterbore 12b. In one embodiment, this angle, denoted as α in FIG. 4, falls within the range of about 30–85 degrees; and is preferably within the range of about 60–85 degrees.

Drip-director 16 is configured to facilitate elution of a mobile phase from the well by funneling it toward a lower opening. In the embodiment of FIG. 4, drip director 16 includes (i) an annular edge or rim 16a disposed above the plane of the upper surface of drip-director plate 14, (ii) depending convergent sidewalls 16b, and (iii) a downspout or outlet port 16c disposed below the plane of the lower surface of drip-director plate 14. The downwardly sloping, inner surface of the convergent sidewalls 16b, between rim 16a and outlet port 16c, defines a conical and/or horn-shaped cavity at the lower region of the well lumen.

As previously mentioned, an upper portion of drip director 16 provides supporting structure adapted to abut a lower peripheral edge region of the filter element. In the embodiment of FIG. 4, such structure takes the form of upper, annular rim 16a. The surface area of the uppermost region of rim 16a (i.e., the portion of rim 16a that directly confronts, and is available to support, the lower peripheral edge region of the filter element) may vary. In one preferred embodiment, the uppermost region of rim 16a defines a narrow circular line. In this embodiment, the contact between rim 16a and filter element 8a is tangential in nature. That is, the region of contact between rim 16a and filter element 8a defines a very thin, circular line. Rim 16a contacts no more than about 15%, and preferably less than about 10%, and more preferably less than about 5% of the bottom surface area of the filter element 8a.

In the illustrated embodiment, the peripheral edge region of filter element 8a is preferably pinched or compressed between shoulder 12d and rim 16a in a manner effective to secure the filter element in place and to press its circumferential side-edge against the inner surface of the column lumen. This arrangement discourages upward or downward movement of the filter element and prevents leakage around its edges.

Figure 5:
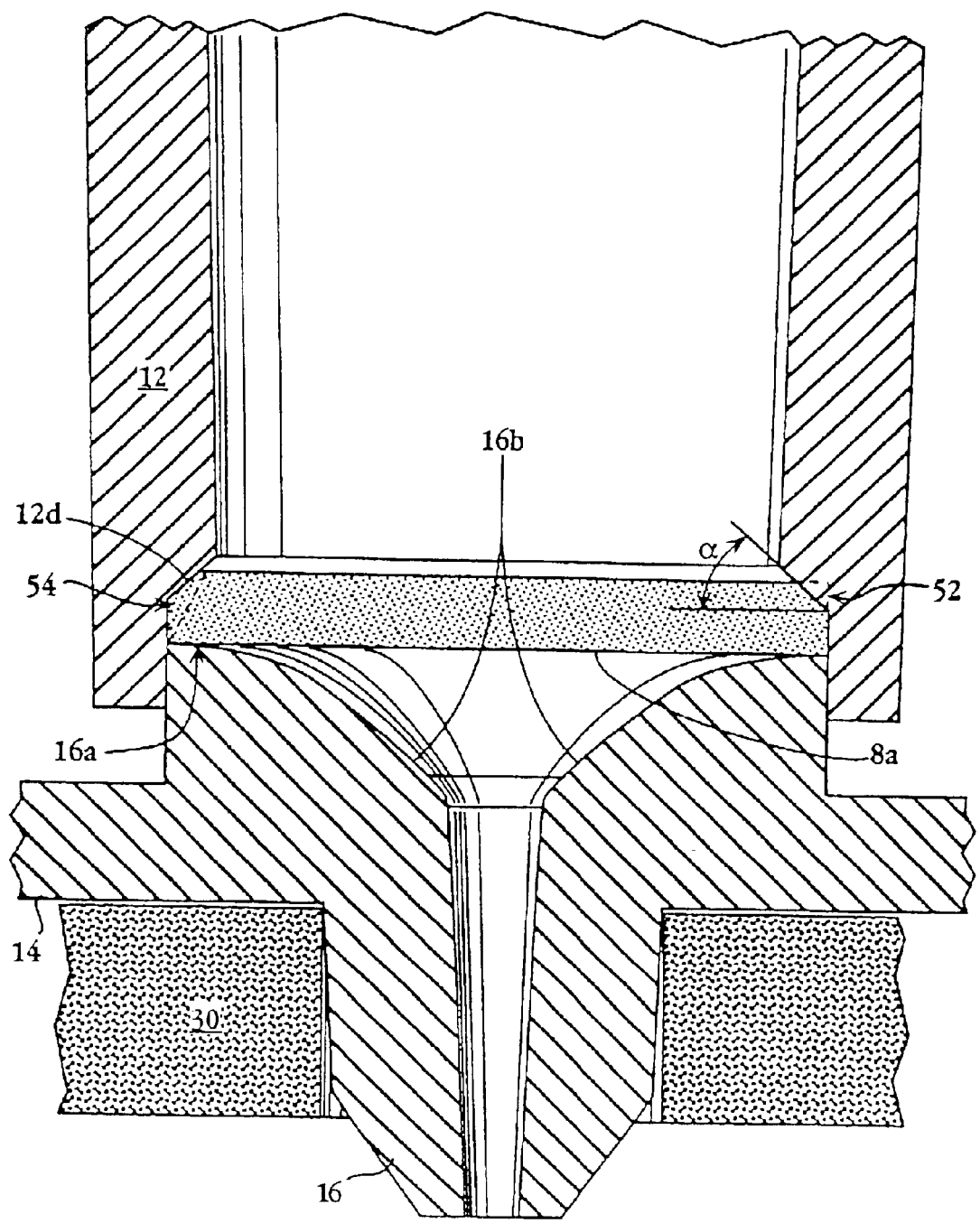
FIG. 5 is a partial side-sectional view showing a microfiltration well constructed in accordance with an embodiment of the present invention.

FIG. 5 is a partial side-sectional view showing a microfiltration well constructed in accordance with one preferred embodiment of the invention. Filter element 8a is compressed between drip-director rim 16a and mini-column shoulder 12d such that the membrane is securely held in place. Further, the compression fit causes the outer circumferential side-edge region of the filter element to press against the inner wall of the column lumen in a manner effective to avoid any bypassing of fluid around the edges of the filter element. Shoulder 12d extends into the mini-column lumen at an angle α of about 45 degrees. Further, the uppermost surface area of rim 16a is minimal, approaching that of a circular line, so that only the outermost perimeter of the filter element's lower surface is in contact therewith.

With continued reference to FIG. 5, both the compression and the dead volume have been estimated for a filter element in one such microfiltration well using the computer-aided engineering package "Pro/ENGINEER" (Release 18), by Parametric Technology Corporation (Waltham, Mass.). The membrane compression for a 950 $\mu$m thick QM-B (Whatman, Inc., Tewksbury, Mass.) filter element having a diameter of 6.88 mm is estimated to be only about 2.6 $\mu$l (area 52 in FIG. 5), and the dead volume for such a filter element is estimated to be only about 3 $\mu$l (area 54 in FIG. 5).

Beneath the filter element 8a, the inner surface of the convergent sidewalls 16b of drip director 16 define a cavity. The cavity is configured to expose the great majority of the filter element's lower surface to open, or free, space. By providing such free space below the filter element 8a (i.e., volume between the drip directors convergent sidewalls 16b and the lower surface of the filter element), preferential flow pathways are avoided.

In another embodiment, to prevent sagging or dislodgement of the filter element into the cavity, the invention provides structure for supporting central points or regions of each filter element. For example, a support buttress may be disposed within the cavity of drip director 16 to provide a resting paint, edge or surface for one or more centrally located regions of the filter element's lower surface. Here, the term "central" refers to those portions of the filter element that are located radially inward of the filter element's peripheral edges; and particularly to those portions that are not held or pinched between a constricted-diameter region in a mini-column and an uppermost rim of a drip director. In a preferred embodiment, the uppermost region of such supportive structure is substantially co-planar with the uppermost portion of the drip-director rim. It should be appreciated that such structure prevents downward sagging or dislodgement of the filter element into the cavity. This is particularly advantageous in connection with filter elements lacking in substantial mechanical strength and/or rigidity.

Figure 6:
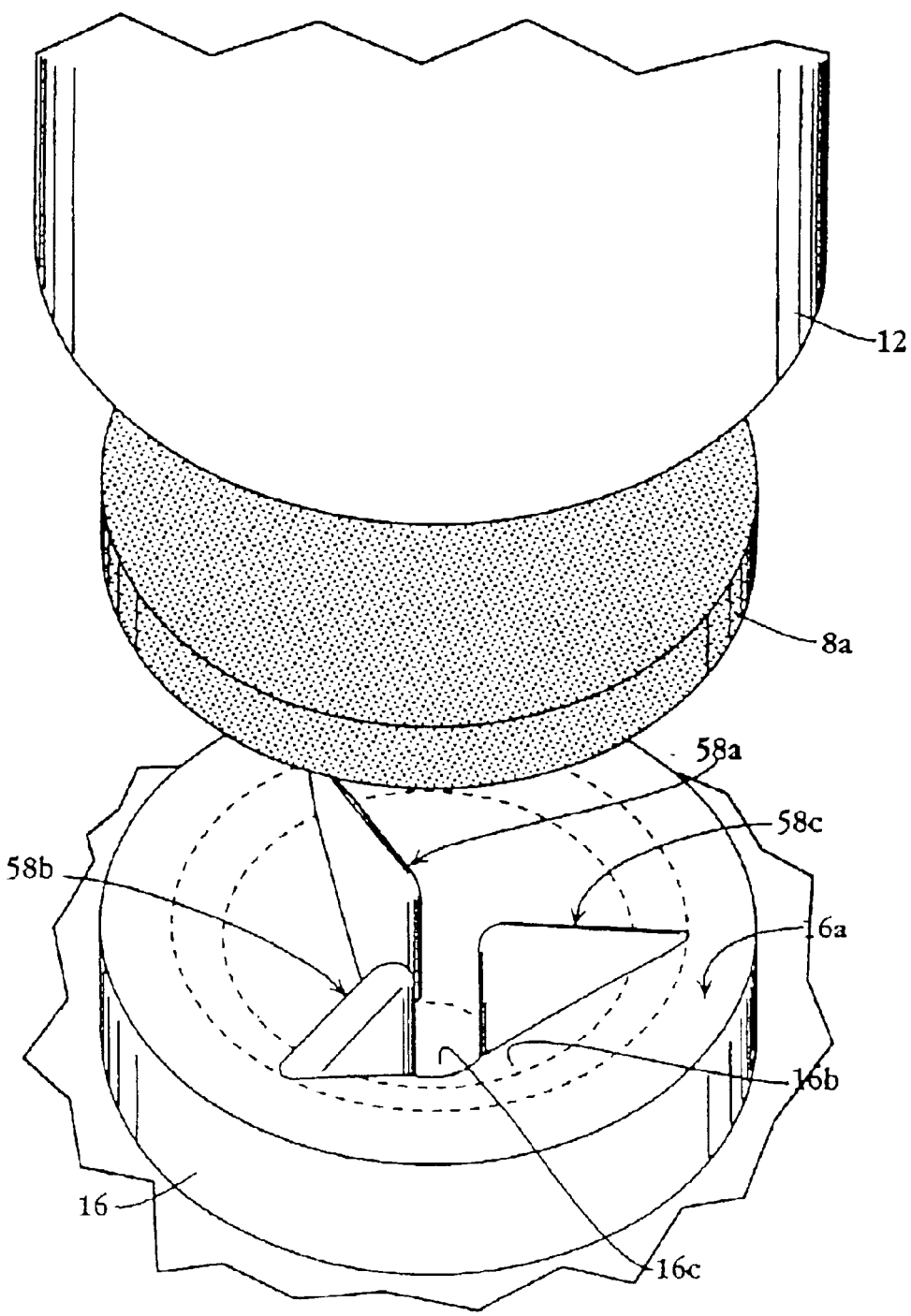
FIG. 6 is an exploded view of a microfiltration well showing membrane support structure in the form of three fin-like support buttresses constructed in accordance with an embodiment of the present invention.
Figure 7:
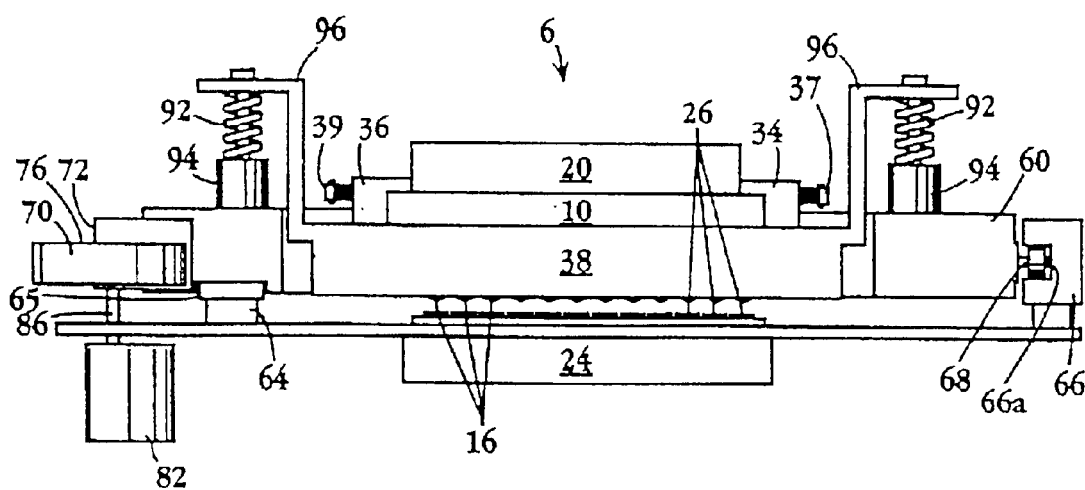
FIG. 7 is an elevational view from one end of a carriage assembly for effecting relative motion between the drip directors of a drip-director plate and the collection wells of a collection plate, according to an embodiment of the present invention.
Figure 8:
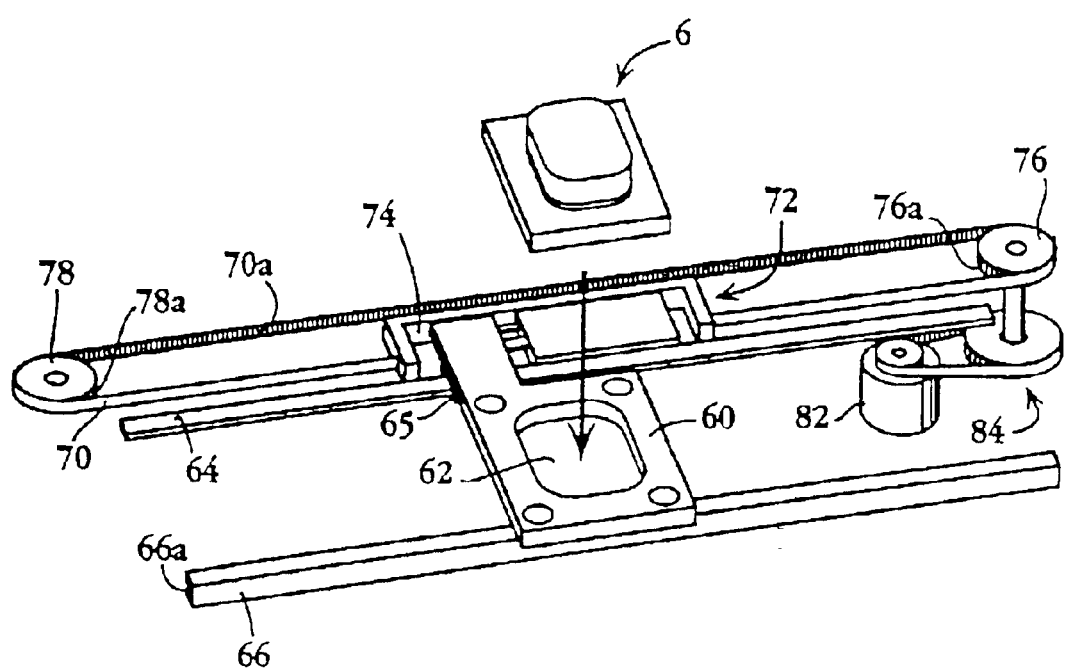
FIG. 8 is a partially exploded, perspective view showing a carriage assembly for effecting relative motion between the drip directors of a drip-director plate and the collection wells of a collection plate, according to an embodiment of the present invention.

In one preferred embodiment, shown in the exploded view of FIG. 6, such supportive structure takes the form of three fin-like support buttresses, denoted as 58a–58c, positioned radially and spaced equidistantly within the cavity of drip-director 16 about central outlet port 16c. It should be appreciated that any other reasonable number of support buttresses, e.g., 4 or 6, may be employed instead. Small portions of the lower surface of filter element 8a rest on top of elongated, narrow, uppermost surfaces or edges of the support buttresses 58a–58c. Preferably, the support buttresses 58a–58c are configured to support the filter element without introducing substantial dead volume or preferential flow in the system. In this regard, the top of each support buttress, proximate the filter element, may be curved, arched, or angled so that the region of contact between the filter element 8a and each buttress is substantially along a line (i.e., tangential in nature). Further, the profile of each support buttress is narrow and streamlined along the direction of fluid flow.

In the illustrated embodiment, the support buttresses 58a–58c are formed integrally with the drip director 16. Alternatively, a plurality of discrete support-buttress arrangements (not shown), formed independently of the flow directors, may be removably positioned or permanently affixed within respective drip directors.

Advantageously, the invention also provides a very efficient and cost-effective method for manufacturing the apparatus described herein. According to one embodiment, a sheet of filter material is positioned between a first plate, having a mini-column formed therein into which a sample can be placed, and a second plate having a discharge conduit, or drip director, with an outlet through which sample may egress. The plates are positioned so that the mini-column is axially aligned with the drip director. The plates are then pressed together so that an upwardly protruding portion of the drip director is snugly received within the lower region of the minicolumn lumen. During the latter operation, a flow pathway is formed, extending from within the mini-column to the outlet of the drip director. Also during the compression step, a piece of filter media is cut from the sheet and positioned across a section of the flow pathway within the mini-column.

The method of the invention is particularly advantageous for constructing a multi-well microfiltration apparatus as detailed above. Therefore, the method of the invention will now be described with reference to the illustrated apparatus. Filter sheet 8 is interposed between the confronting surfaces of column plate 10 and drip-director plate 14, as shown in FIG. 2. The plates 10, 14 are arranged so that each mini-column 12 is in axial alignment with a corresponding drip director 16. The plates 10, 14 are then pressed together to achieve a configuration substantially as shown in FIG. 3. During the compression step, an upper annular rim 16a of each drip director 16 acts as a die to punch out a piece of filter media 8a (e.g., in the form of a disc) from the filter sheet. Furthermore, compressing the drip director 16 against the mini-column 12 secures the filter element in place within the mini-column lumen. As a result, an outer, peripheral edge portion of filter element 8a is pinched between an upper, annular rim 16a of drip director 16 and an internal, annular shoulder 12d of mini-column 12. The drip director 16 and mini-column 12 are then secured together by any suitable means. For example, an ultrasonic weld or a tongue-in-groove arrangement can hold the mini-columns 12 and drip directors 16 together, as discussed above.

A further aspect of the present invention pertains to a multi-well microfiltration arrangement that provides for the flow of filtrate out of each well, while avoiding cross-contamination due to aerosols or splattering.

As previously described, the collection-well array corresponds to the drip-director array, with each drip director disposed directly over a receiving or collection well. The collection-well plate, in turn, is adapted to fit within an open reservoir of a lower vacuum chamber, with the collection wells extending down into the reservoir. Upon establishing a suitable vacuum in the lower chamber, filtrate will flow from each microfiltration well and into corresponding collection wells. In accordance with this aspect of the invention, means are provided for discouraging filtrate-associated aerosols and residues present at any one well from traveling to, and potentially contaminating neighboring wells. Such means can include, for example, a cross-flow restrictor, also referred to as an aerosol guard, composed of a substantially aerosol-impervious material, interposed in the region between the upper surface of collection plate and the lower surface of drip-director plate. While limiting the passage of aerosols and filtrate-associated residues, the cross-flow restrictor is adapted to permit a vacuum to be drawn therethrough.

With particular reference to the embodiment of FIGS. 2 and 3, a sheet-like cross-flow restrictor 30 is provided with an array of passages 32 complementary to the collection-well and drip director arrays that permit filtrate to pass from each microfiltration well 18 to a corresponding collection well 26. Except for such passages, cross-flow restrictor 30 substantially fills the area between the confronting faces of the drip-director and collection-well plates (14, 24). In this way, well-to-well movement of aerosols over the collection plate 24 is substantially blocked. Consequently, the risk of cross-contamination presented by aerosol movement is substantially reduced. Additionally, aerosols formed at any one collection well that inadvertently pass through the cross-flow restrictor (i.e., those that are not effectively blocked or trapped) will be pulled by the vacuum source through an adjacent aperture 28 down to the region below plate 24 without passing over the openings of neighboring collection wells, as described more fully below.

Embodiments of the present invention contemplate attachment of the cross-flow restrictor to the upper face of the collection-well plate 24 or to the lower face of the drip-director plate 14. Such attachment may be made by any suitable means, e.g., using fasteners, welds and/or one or more adhesives, such as tapes, gums, cements, pastes, or glues. Instead of attaching the aerosol guard to a plate, the aerosol guard may simply be sandwiched between the confronting surfaces of the plates and maintained in place, for example, by frictional and/or compressive forces.

The aerosol guard may be formed as a single sheet, e.g., about 0.10" to 0.15" thick, or, attentively, it may be formed of two or more sheets, e.g., each about 0.060" to 0.065" thick, arranged in layers. In one preferred embodiment, a single-layer aerosol guard made of a porous hydrophilic polymer having compliant characteristics, such as ethyl vinyl acetate (EVA) or the like, is attached to the lower face of the drip-director plate using a pressure sensitive adhesive. Another embodiment contemplates a multi-layered construction, including: (i) a conformant layer comprising a foam pad, about 0.062" thick and having a pressure sensitive adhesive on both faces, and (ii) a porous, UHMW (ultra-high molecular weight) polymer layer, about 0.062" thick, that is permeable to air but substantially impermeable to aerosols. In this latter embodiment, the conformant layer is attached to the lower face of the drip-director plate and then the UHMW polymer layer is attached to the conformant layer.

Other materials (i.e., hydrophobic, non-polymeric, etc.) may be used in forming the compliant aerosol guard of the present invention, provided only that the material(s) effectively limits the passage of aerosols, while permitting the drawing of a vacuum therethrough.

In another embodiment, the means for avoiding cross-contamination due to the well-to-well movement of aerosols includes vents or apertures 28 extending through the surface of collection plate 24. In one preferred embodiment, at least one such aperture is disposed near each collection well. It should be appreciated that a reduced pressure applied from below the plate will extend through the apertures to the microfiltration wells.

Any number and spatial configuration of apertures may be utilized, provided only that the region between each drip-director outlet and corresponding collection well is disposed in fluid communication (i.e., permissive of a vacuum) with the region below the collection plate along a pathway that does not pass over the openings of neighboring wells. For example, an aperture may be provided centrally within a group of four wells, with the wells being disposed about the corners of a quadrilateral. By providing 24 of such 4-well groupings, each well of a standard 96-well arrangement could be provided with a vent or aperture adjacent thereto.

Alternatively, the number of apertures may equal or exceed the number of collection wells, with each well having one or more closely associated apertures proximate thereto. For example, a 96-well collection plate could be provided with at least 96 apertures arranged so that each well has at least one closely-associated aperture. In this regard, the apertures may be laid out, for example, in a 12×8, or 13×9, regular rectangular array.

As previously noted, apertures 28 permit fluid communication between the regions above and below the collection-well plate 24. Upon evacuating lower vacuum chamber 29, a vacuum will be established reaching from exit port 51 to the region between each microfiltration well and a corresponding collection well. Particularly, the vacuum will pull along flow pathways extending from each microfiltration well 18 into the interface region between the confronting surfaces of drip-director plate 14 and collection-well plate 24. The vacuum flow pathways then will cross downward through the collection plate's surface 25, by way of respective vents 28, to the open reservoir of chamber 29. Here, the vacuum flow pathways will extend along the lower chamber until reaching exit port 51. Large, blackened arrows illustrate exemplary vacuum flow pathways in FIG. 3. Advantageously, aerosols arid filtrate residues that become entrained in the vacuum flow are largely directed away from each collection well area and out of the system without passing over neighboring collection wells. Also, it should be appreciated that the vacuum pathways are directed in such a manner as to encourage a flow that is largely downward and laminar in nature. Cross-flow, and thus turbulence, is greatly minimized compared to most conventional arrangements.

The illustrated embodiments show a cross-flow restrictor 30 used in combination with a vented collection-well plate 24, as just described. Notably, the cross-flow restrictor 30 covers the apertures 28, so that a vacuum pathway extending from the region between each microfiltration well 18 and corresponding collection well 26 to the region below the collection-well plate 24, via a nearby aperture 28, must pass through the cross-flow restrictor 30. Since the cross-flow restrictor 30 allows a vacuum to be drawn therethrough, but discourages the passage of aerosols, filtrate-associated aerosols are substantially separated (i.e., filtered out by the cross-flow restrictor) from the drawn vacuum and, thus, the potential for well-to-well movement of aerosols over the collection plate's surface 25 is even further reduced.

Instead of utilizing a unitary cross-flow restrictor for a plurality of drip directors and collection wells (e.g., a sheet having a plurality of circular perforations extending therethrough), as described above and shown in the accompanying drawings, an alternative embodiment contemplates a plurality of individual collar or skirt-like cross-flow restrictors. In horizontal cross-section, such individual cross-flow resections can be of any suitable shape, e.g., annular, elliptical, oblong, etc. In one embodiment, each individual cross-flow restrictor co-axially and laterally surrounds the region between one drip director and a corresponding collection well. Such cross-flow restrictors can be formed of a substantially rigid material, e.g., like that of the drip-director plate, or they can be formed of a compliant, porous hydrophilic material, e.g., a polymer such as ethyl vinyl acetate (EVA) or the like. In one embodiment, a plurality of substantially rigid, annular or elliptical cross-flow restrictors are integrally molded with one of the trays, e.g., depending from the lower surface of the drip-director plate and extending down toward the collection-well plate, about respective drip directors. Further, each such rigid cross-flow restrictor is configured to allow a vacuum drawn from beneath a collection plate, situated under the drip-director plate, to extend to the region proximate the encircled drip director. In this regard, each cross-flow restrictor can be configured to encompass, in addition to a corresponding collection well, an adjacent aperture leading to the region below the collection plate. That is, the cross-flow restrictor can extend around both a corresponding collection well and an adjacent aperture. In an alternative embodiment, the cross-flow restrictor extends only around its corresponding collection well. That is, the cross-flow restrictor does not additionally encompass an adjacent aperture. Rather, in this embodiment, a small through-hole formed in the cross-flow restrictor, proximate the aperture, permits fluid communication between the aperture and the region proximate the drip director. It should be appreciated that, like the previously-described sheet-like cross-flow restrictor 30, the individual cross-flow restrictors shield against filtrate spattering and undesirable lateral movement of aerosols across the upper surface of the collection-well plate that can result in cross-contamination.

As previously mentioned, it is noteworthy that the vacuum flow pathways established between the regions above and below the collection-well plate, in all of the embodiments described herein, are routed in a manner that encourages a largely laminar and downward flow (including any entrained gases and/or aerosols). Compared to most conventional arrangements, horizontal flow over the upper surface of the collection-well plate is greatly minimized. Not only is this the case in the regions proximate the microfiltration and collection wells, but it is also the case for the peripheral-edge regions of the plates. In this regard, and with particular reference to the embodiment of FIG. 3, the contact between the inwardly extending flap 44a of stepped gasket 44 and the top of ridge 48 of the collection-well plate 24 is such that airflow therebetween is obstructed or baffled. Thus, upon evacuating the lower vacuum chamber 29, gases located above the stepped gasket 44, in the region denoted by arrow 46, will be drawn into the lower vacuum chamber via vent 28. Gases in the space under the lower surface of stepped gasket 44, denoted generally by the arrow 47, on the other hand, will be drawn into the lower vacuum chamber via a gap 49 provided between the collection-well plate and the surface 50 about vacuum chamber 29. By limiting the extent of horizontal airflow across the collection-well plate in this way, turbulence resulting from cross flow along the periphery of the arrangement is minimized.

An additional means for avoiding cross-contamination due to well-to-well movement of aerosols, as well as filtrate splattering, relates to the positioning of each drip director's lower opening relative to the upper rim, or lip, of a corresponding collection well. According to this feature, the outlet port 16c of each drip director 16 extends downwardly from the drip-director plate 14 so as to enter into a corresponding collection well 26. In this regard, the lower portion of each drip director 16 has a diameter that enables it to register with the open top of a corresponding collection well 26 in the collection plate 24. As shown in the embodiment of FIG. 3, the outlet port 16c of each drip director 16 is situated below the upper rim or lip of a corresponding collection well 26. By placing the outlet port 16c at a region that is laterally surrounded by the inner sidewalls of the collection well 26, much of the aerosol generated during filtration will impact upon the collection-well walls, as opposed moving laterally over toward a neighboring collection well. As an additional advantage, such placement of the drip-director outlets helps to reduce filtrate splattering.

In a related aspect, the present invention provides a method for avoiding cross-contamination due to well-to-well movement of aerosols in a multi-well microfiltration system. According to one embodiment, the method includes the steps of:

(i) providing an array of microfiltration wells (containing fluid samples) over a collection-well tray supporting a corresponding array of collection wells;

(ii) drawing a vacuum along flow pathways extending (a) from each microfiltration well (b) downward through a plane defined by an upper surface of the collection tray at a point at, or adjacent, a corresponding collection well (c) to a region beneath the collection tray, thereby causing a filtrate to flow from each microfiltration well and into corresponding collection wells: and (iii) obstructing aerosols formed from the filtrate at any one microfiltration well from moving across the upper surface of the collection tray to a non-corresponding collection well, thereby limiting cross-contamination.

It should be appreciated that the apparatus described above is particularly well suited for carrying out this method. For example, a vacuum chamber, such as lower chamber 29 shown in FIG. 3, may be connected to a low pressure source, such as a vacuum pump (not shown), for establishing a pressure differential across filter elements 8a, 8b disposed in microfiltration wells 18. The reduced pressure, then, will cause filtrate to emanate from drip directors 16. Aerosol guard 30 provides a means to limit filtrate-associated aerosols formed from the filtrate at any one microfiltration well 18 from moving across the upper to surface 25 of collection-well plate 24 to a neighboring collection well. Apertures 28, extending through the surface 25 of collection plate 24, permit the vacuum to extend between each microfiltration well and the region below the collection-well plate 24 without having to pass over the openings of neighboring collection wells.

When evacuating the lower chamber, it is advantageous to slowly change (ramp) the pressure to a desired value, combined with the utilization of very low pressures (e.g., less than about 2 psi, and preferably less than about 1 psi), in to further reduce the potential for cross-contamination, as by aerosols. For example, in going from ambient pressure to a value within the range of about 0.75 to about 2 psi, a ramp period of about 2–3 seconds is employed.

Another aspect of the present invention pertains to a multi-well microfiltration arrangement that provides for the flow of filtrate from each well, while avoiding cross-contamination due to pendent drops which may adhere to the drip directors of the various microfiltration wells. As previously mentioned, such pendent drops can fall into neighboring collection wells when moving the drip-director plate over the collection-well plate.

According to one embodiment, a microfiltration well is evacuated in the direction of its upper opening, thereby pulling any pendent drops of fluid hanging from its drip director back up into the well. To accomplish the evacuation, a pressure control source, e.g., a vacuum pump, in communication with an upper region of the mini-column is operable to evacuate the mini-column in the direction extending from the drip director to the upper opening.

Another embodiment provides for "touching off" the tips of the drip directors to remove pendent drops of filtrate that might hang off of the drip directors. In this regard, the drip director outlets of all the microfiltration wells are simultaneously brought into contact with the inner sidewalls of corresponding collection wells.

Means are provided for effecting relative motion between the drip-director plate and the collection-well plate for simultaneously moving the discharge conduits into and out of contact with inner walls of respective collection wells. In one embodiment, such means are operable to shift the collection-well plate along a plane substantially orthogonal to the longitudinal axes of the microfiltration wells, while the microfiltration wells themselves are maintained in a substantially fixed position. In another embodiment, the means for effecting relative motion are operable to shift the microfiltration wells along a plane substantially orthogonal to the longitudinal axes of the collection wells, while the collection wells are maintained in a substantially fixed position.

An exemplary arrangement for effecting relative motion is depicted in FIGS. 7 through 10. Worth initial reference to FIGS. 7 and 8, an L-shaped carriage, as denoted by the reference numeral 60, is provided with a central opening 62 configured to receive and support a multi-well microfiltration assembly, indicated generally as 6, from above. Below carriage 60, a collection plate 24 having an array of collection wells 26 is supported in a lower vacuum chamber (not shown).

Carriage 60 is mounted on a pair of parallel longitudinal carrier rails for reciprocal linear motion along a first, substantially horizontal, axis. In the illustrated embodiment, one of the carrier rails is a linear bearing rail, denoted as 64, which supports the carriage 60 via an interposed linear bearing member 65 attached to the lower surface of the carriage 60 toward one lateral edge. The other carrier rail is a U-shaped bearing guide, denoted as 66, that receives a bearing wheel 68, extending laterally outward from the other edge of the carriage 60, in an elongated track or slot 66a.

Carriage 60 is moved along the rails 64, 66 by a belt assembly comprised of a flexible belt 70 having its ends attached at each longitudinal end of a U-shaped bracket 74 forming a part of a spring-loaded motion-control mechanism 72, described more fully below. Belt 70 is passed around a driven 76 roller and an idler roller 78, disposed proximate longitudinally opposing ends of the carrier rail arrangement. To prevent against slippage, the belt may be provided with teeth 70a adapted for mating engagement with complementary sets of teeth 76a, 78a on the rollers.

Driven roller 76 is in mechanical communication with a motor, such as 82, through a power train assembly, as indicated generally by the reference numeral 84. When motor 82 is energized, belt 70 will move, causing carriage 60 to slide along the carrier rails 64, 66, with the direction of movement depending on the rotation of the drive shaft 86 extending from motor 82. Motor 82 may be of any suitable, known type, e.g., a stepper motor, servo motor, or similar device.

One preferred embodiment of the present invention contemplates the use of a stepper motor to move belt. By way of background, a stepper motor is a specialized type of motor that moves in individual steps. Unlike servo motors, the position of a stepper can be determined without the need for expensive encoders to check its position. Stepper motors are much more cost-effective than servo systems due to their simplified control and drive circuitry. There are no brushes to replace in a stepper motor, reducing the frequency for maintenance. Owing to their ease of use and relatively low cost, steppers are often preferred over servo motors for many modem computerized motion control systems.

According to this embodiment of the invention, a control system is provided to operate the stepper motor in a desired fashion. For example, a microcontroller, such as a Motorola 68332, may be utilized to control the motor using conventional techniques.

As previously noted, stepping the motor 82 causes belt 70 to move around rollers 76, 78, with the direction of movement dependent upon the direction of rotation of the motor's shaft 86. Movement of belt 70, in turn, causes carriage 60 to slide along guide rails 64, 66, thereby shifting the drip director array 16 laterally with the respect to the collection well array 26. If the drip directors 16 are positioned so that they extend into respective collection wells 26, sufficient stepping in a given direction will cause the drip directors 16 to engage the upper, inner surfaces of the collection wells 26, as shown in the sectional views of FIGS. 9(A)–9(C). In this way, pendent drops of filtrate hanging from the drip directors 16 are "touched off" to the inner surfaces of respective collection wells 26. Similarly, upon reversing the stepping direction, the drip directors 16 can be moved to engage the upper, inner surfaces on the opposing side of the collection wells 26 to further ensure effective touching off of pendent drops.

As previously mentioned, alternative embodiments of the invention contemplate the use of a servo motor to move the belt. In one such embodiment, a means for providing positional feedback, such as an encoder (not shown), is provided in order to track the position of the servo motor.

Carriage additionally supports means for moving and positioning the microfiltration arrangement 6 along a second, generally vertical, axis. With particular reference to the embodiment of FIG. 7, a vertical-positioning mechanism is disposed on the upper surface of carriage along each lateral side of the microfiltration arrangement. Each vertical-positioning mechanism includes (i) lift springs, such as 92, that provide a continuous, upwardly-directed force tending to raise the microfiltration arrangement 6 to an elevated position whereat the drip directors 16 fully clear the upper lips of the collection wells 26, and (ii) fluid cylinders, such as 94, that are operable to lower the microfiltration arrangement 6, against the force of the lift springs 92, to a seated position whereat each drip director 16 extends into the upper region of a respective collection well 26. At its fully seated (lowered) position, the microfiltration arrangement 6 forms a seal with the lower vacuum chamber (not shown).

Both the springs 92 and the fluid cylinders 94 engage, at their upper ends, handles, denoted as 96, that extend upwardly and outwardly from each lateral side of the microfiltration arrangement's supporting frame 38. In one embodiment, the spring/cylinder arrangements are operable to hold the microfiltration arrangement at any one of three positions: (i) an up or travel position, (ii) a touch-off position, and (iii) a down or seal position.

The touch-off operation may be carried out with the microfiltration arrangement 6 disposed at any position along the second (vertical) axis, provided only that the drip directors 16 extend at least partially down into the collection wells 26. In one embodiment, touching off of the drip directors 16 to the inner sidewalls of the collection wells 26 is effected with the microfiltration arrangement 6 slightly raised above its fully seated position so that the lowermost regions of the drip directors 16, proximate their outlets 16c, will abut the inner surfaces of the collection wells 26.

Figure 9A:
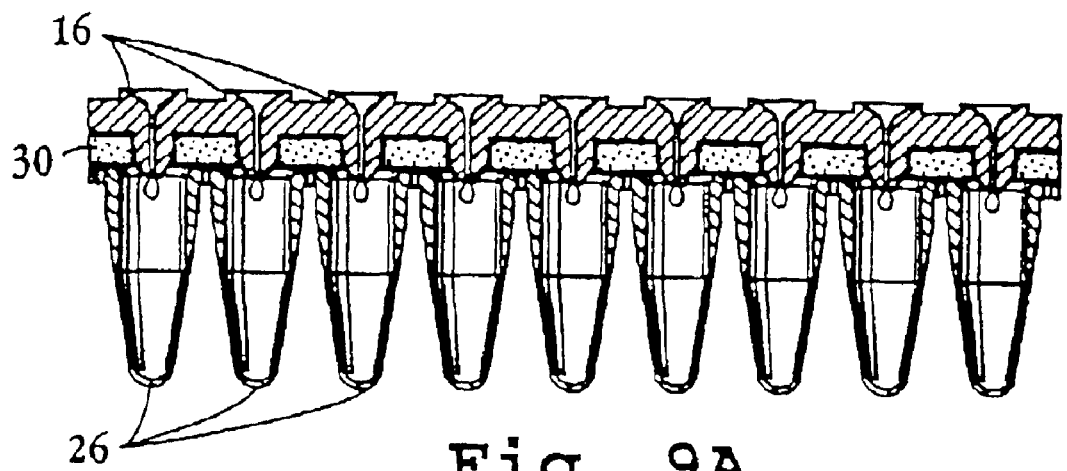
FIGS. 9(A)–9(C) are side cross-sectional views showing a touch-off operation whereby a plurality of drip directors is laterally shifted to the right and to the left such that the drip director outlet regions simultaneously abut inner sidewalls of a plurality of corresponding collection wells.
Figure 9B:
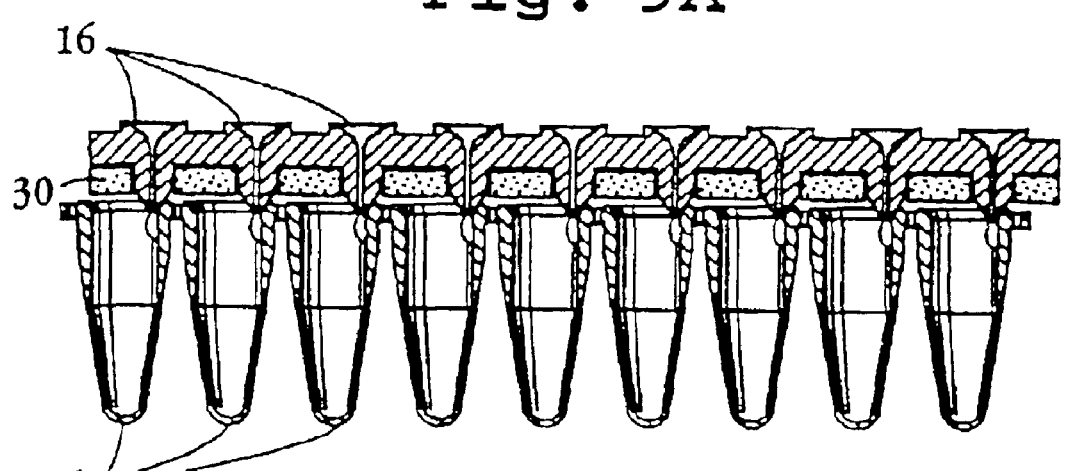
Figure 9C:
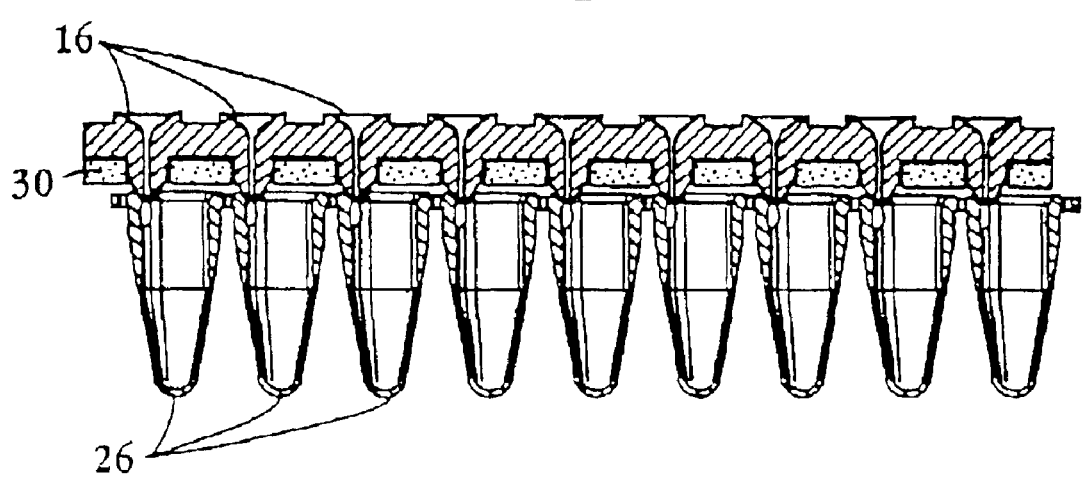

The region of each drip director 16 proximate its outlet may be shaped, e.g., angled or chamfered about its lower circumference, to promote the localization of any pendent drops of filtrate to certain regions of the drip director 16 and to optimize contact between such regions with the inner sidewall of a corresponding collection well 26 during touch off. Similarly, the upper region of each collection well 26 may also be shaped, e.g., in a manner complementary to (i.e., matching) a shaped drip director 16, so that adequate contact is made between these elements during touch off for substantially ridding the drip director 16 of any pendent drops of filtrate. In one preferred embodiment, as can be seen in FIGS. 9A–C, the upper, region of each collection well is formed with an outwardly angled inner sidewall that matches an inwardly angled outer surface along the lower region of a corresponding drip director, thereby providing a substantial abutting surface between these elements during a touch-off operation.

As previously described, the discrete quantity of angular rotation imparted to shaft 86 each time stepper motor 82 is stepped is ultimately translated into a given length of linear movement by bracket 74. For example, stepping the motor 82 once may cause bracket 74 to move ½" in a particular direction. It should be appreciated that the minimum number of steps required of stepper motor 82 to effect a touch off may cause the drip directors 16 to move farther than what is necessary. That is, the drip directors 16 might be moved into engagement with the inner walls of the collection wells 26, with continued pressure to move beyond the inner walls. As described next, such linear overshoot can be advantageous, as it can assist in the removal of pendent drops. It should be appreciated that it is desirable to move the drip directors to a suitable position against the collection-well sidewalls (e.g., in firm abutment with the sidewalls) in order to effectively encourage the removal of pendent drops. By providing a suitable amount of linear overshoot into the sideward movement of the drip directors, such positioning can be ensured (i.e., the drip directors will not fall short of the sidewalls), notwithstanding various minor positional inaccuracies inherent in the arrangement. Thus, by providing for a reasonable amount of linear overshoot, the sidewalls themselves determine the final position of the drip directors. It is also desirable to keep the torque relatively low, thereby preventing clogging of the motor. Further, it is desirable to absorb or compensate for some of the linear overshoot to avoid overstressing the drip directors 16 and/or the collection wells 26.

In these regards, one embodiment of the invention contemplates the use of a spring-loaded motion-control mechanism 72 in the mechanical linkage system between the motor 82 and the carriage 60. The motion-control mechanism 72 ensures accurate positioning of the drip directors in abutment with the sidewalls, while absorbing excess linear motion beyond the amount required to shift the drip directors 16 into contact with the inner sidewalls of the collection wells 26. As an additional advantage, the motion-control mechanism 72 provides a damping resistance to sliding movement of the carriage 60 along the rails 64, 66.

In one embodiment, the motion-control mechanism includes a spring disposed such that movement of the carriage in either direction along the first axis will put the spring under compression. With particular reference to the partially schematic top plan views of FIGS. 10(A)–(C), the U-shaped bracket 74 that forms a part of the belt assembly is rigidly connected to a housing 101 containing large and small bores, respectively indicated generally as 102 and 108. Bore 102 has a large-diameter portion 102a and a small-diameter portion 102b, separated by a radial step 102c. A stepped-diameter shaft, indicated generally as 104, having a large-diameter portion 104a and a small-diameter portion 104b, separated by a radial step 104c, passes through bore 102 and rigidly attaches, at its large-diameter end, to an extended-arm portion 60a of the L-shaped carriage 60. A guide pin 106, which assists in maintaining the substantially horizontal orientation of carriage 60, rigidly attaches to the extended arm portion 60a of carriage 60 at one end and is received in small bore 108 at its other end. Inside the large-diameter portion 102a of bore 102, a spring 110 concentrically mounts the small-diameter portion 104b of shaft 104 between a pair of spaced washers, denoted as 112 and 116. The two washers 112, 116 are concentrically mounted for sliding movement along the small-diameter portion 104b of stepped shaft 104. Spring 110 urges the two washers 112, 116 toward opposite, extreme ends of the small-diameter portion 104b of shaft 104. A fixed-position washer 114 is seated within a circumferential groove (not shown) formed in the small-diameter portion 104b of shaft 104 near its free end.

Figure 10A:
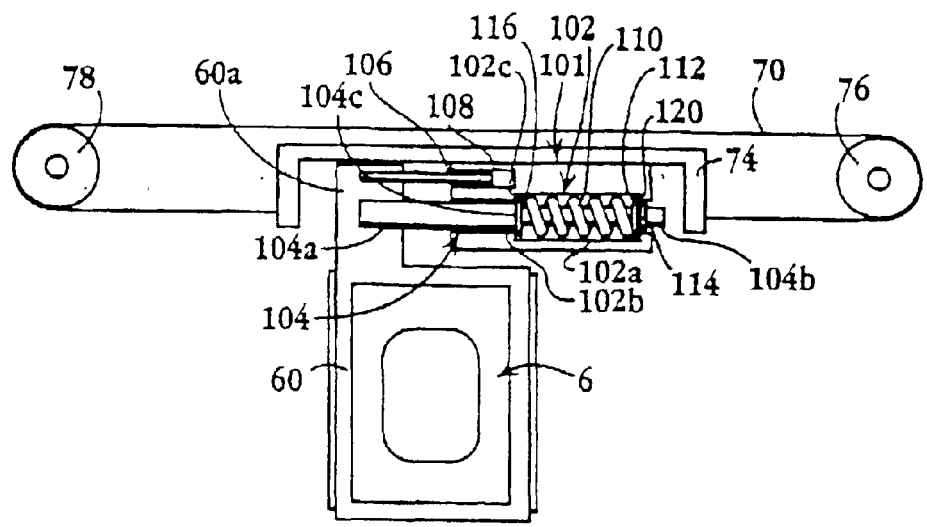
FIG. 10(A) is a partially schematic top plan view showing a spring-loaded touch-off mechanism in its normal, or neutral, position.
Figure 10B:
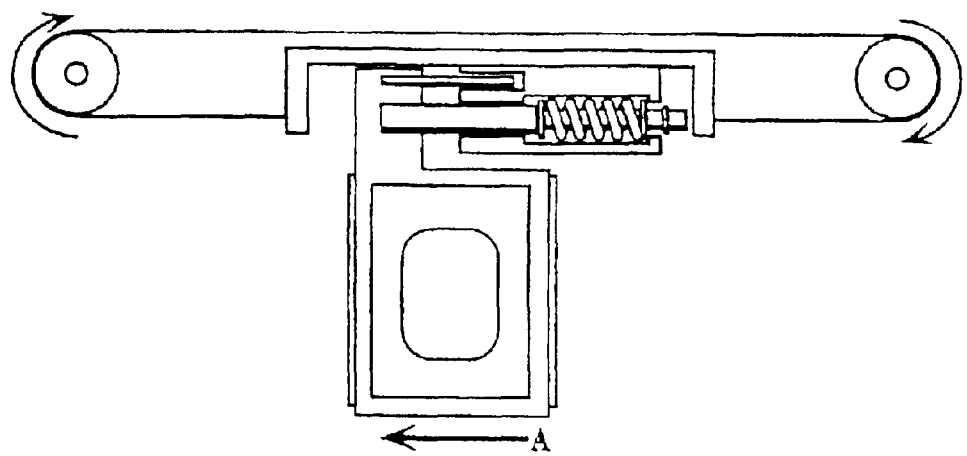
FIG. 10(B) is a partially schematic top plan view showing the spring-loaded touch-off mechanism of FIG. 10(A) in a first, shifted position.

When belt 70 moves U-shaped bracket 74 in the direction indicated by the arrow "A," in FIG. 10B, bore 102 slides along shaft 104 in a direction toward the extended arm 60a of carriage 60. As a result, an annular lip 120 that extends radially inward at the end of bore 102 acts against an annular, peripheral region of washer 112, causing the washer 112 to slide along the small-diameter portion 104b of stepped shaft 104, thereby compressing spring 110. When the compression force overcomes the pre-loaded retaining force, carriage 60 will then shift in the same direction (direction "A").

Figure 10C:
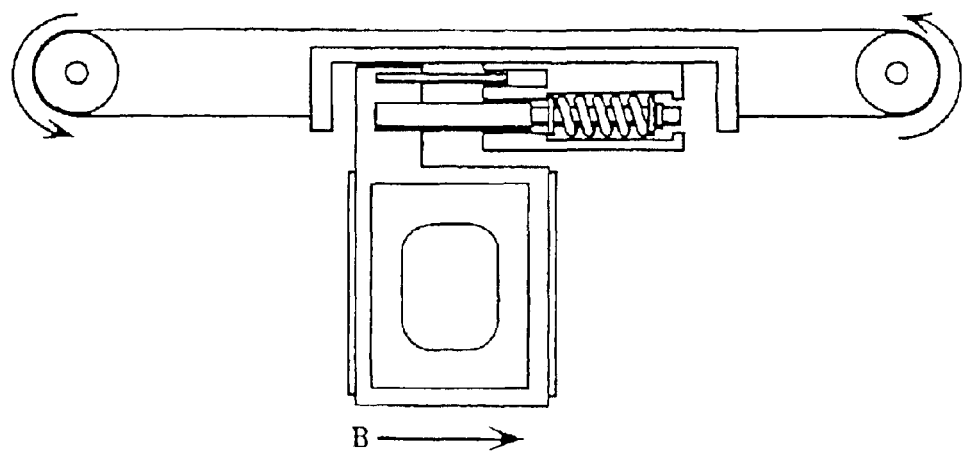
FIG. 10(C) is a partially schematic top plan view showing the spring-loaded touch-off mechanism of FIGS. 10(A)–10(B) in a second, shifted position.

When belt 70 moves U-shaped bracket 74 in the direction indicated by the arrow "B," in FIG. 10C, bore 102 slides along shaft 104 in a direction away from the extended arm 60a of carriage 60. As a result, the radial step 102c of bore 102 acts against an annular, peripheral region of washer 116, causing the washer 116 to side along the small-diameter portion 104b of stepped shaft 104, thereby compressing spring 110. When the compression force overcomes the pre-loaded retaining force, carriage 60 will then shift in the same direction (i.e., direction "B").

In one embodiment, spring 110 provides a pre-load force of about 1 pound. Thus, the force provided by the stepper motor 82 will not be effective to move the carriage 60 until the threshold of about 1 pound is overcome. Advantageously, the arrangement provides (i) a constant-hold mode at the center, or neutral, position, and (ii) a constant-force mode for effecting touch off. The spring 110 provides compliance in the system, e.g., allowing touch off to start at 1 pound and end at 1.2 pounds.

With reference to the apparatus as described above, one preferred embodiment of the present invention contemplates the following steps:

(i) microfiltration arrangement 6 is loaded onto carriage 60 and clamped in place;

(ii) carriage 60 is centered over a lower vacuum chamber 29;

(iii) microfiltration arrangement 6 is lowered to its seated position (e.g., by retracting fluid cylinders 94) and sealed over the lower vacuum chamber 29;

(iv) a robot (not shown) lowers upper vacuum chamber 20 against the top of microfiltration arrangement 6 and, optionally, applies a downward force, e.g., about 5 pounds, to the stacked arrangement;

(v) lower vacuum chamber 29 is evacuated (e.g., at about 0.5–3 psi) to effect elution/purification;

(vi) carriage 60 is raised slightly from its fully seated position to a touch-off height whereat only the lowermost regions of the drip directors 16 extend below the upper lips of the collection wells 26;

(vii) motor 82 is stepped in a forward direction to touch off the drip directors 16 to a sidewall of the collection wells 26;

(viii) motor 82 is stepped in a reverse direction to touch off the drip directors 16 to the opposing inner sidewall of the collection wells 26;

(ix) forward and reverse stepping of motor 82 is repeated to perform each of the touch-off steps once more;

(x) carriage 60 is re-centered over lower vacuum chamber 29;

(xi) microfiltration arrangement 6 is lowered to its seated position and sealed over lower vacuum chamber 29;

(xii) optionally, the robot can apply a downward force, e.g., about 5 pounds, to the stacked arrangement;

(xiii) upper vacuum chamber 20 is evacuated to effect a pull-back of pendent drops (e.g., at about 0.1–0.3 psi);

(xiv) microfiltration arrangement 6 is raised to its fully elevated position so that the drip directors 16 fully clear the collection wells 26; then (xv) carnage 60 is moved to next station.

Figure 16:
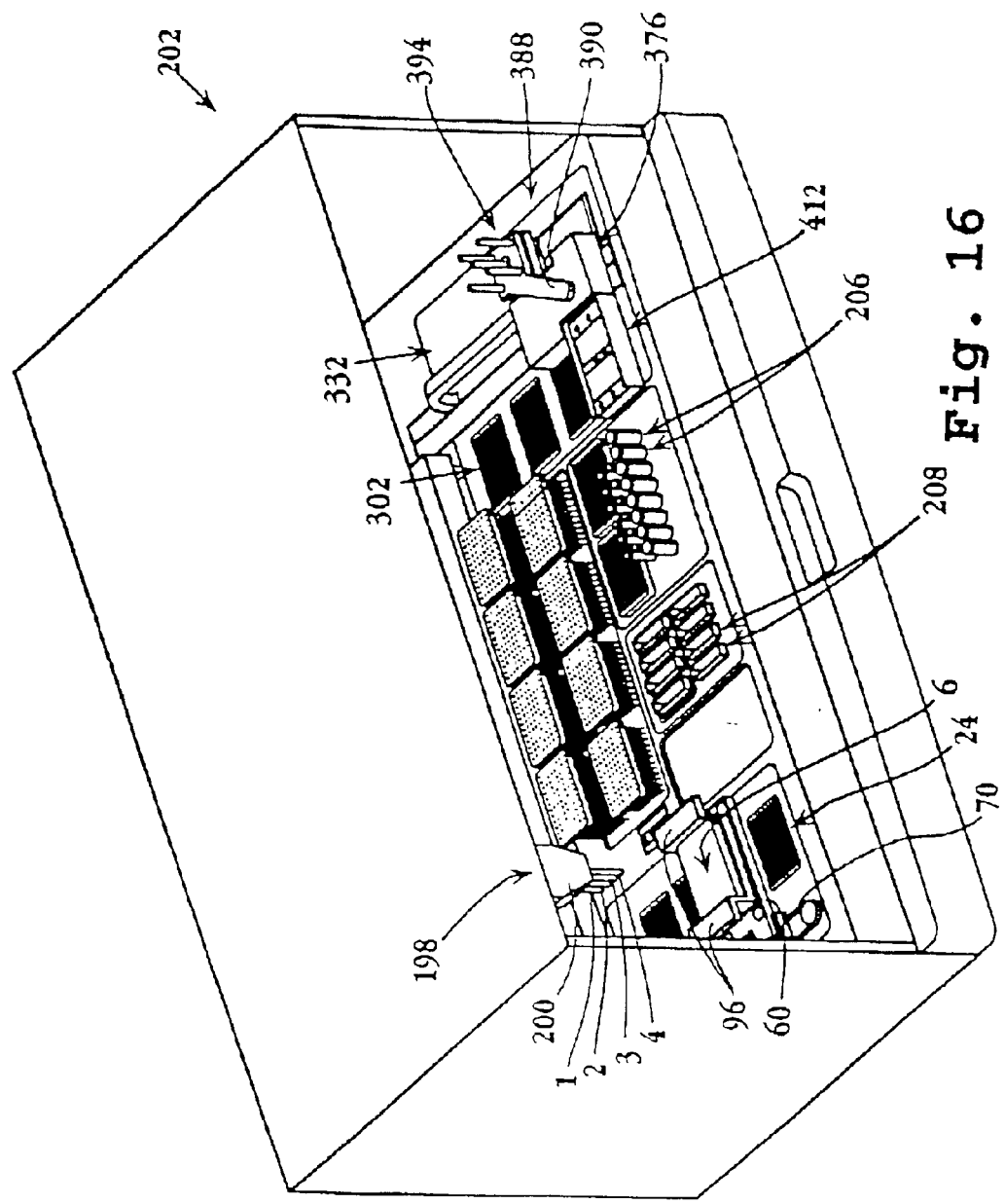
FIG. 16 is a perspective view showing an automated high-throughput sample preparation workstation, including, for example, a microfiltration apparatus, cross-contamination control arrangements, collection-well covering and heat-sealing assemblies, and associated components and reagents, in accordance with the teachings of the present invention.

FIG. 16 shows an automated high-throughput sample preparation workstation 202, including, for example, a microfiltration apparatus, cross-contamination control arrangements, as well as collection-well covering and heat-sealing assemblies (described below), and associated components and reagents, in accordance with the teachings of the present invention. As illustrated, several collection trays can be provided in adjacent vacuum chambers arranged in a side-by-side fashion near one end of the workstation. For example, a closed-bottom collection tray, such as tray 24, can sit in each of the two endmost vacuum chambers, while open-bottom collection trays can sit in the two center vacuum chambers. Carriage 60 can then carry a microfiltration arrangement 6 successively from one vacuum chamber to the next. For instance, an initial collection of filtrate can take place at the vacuum chamber holding closed-bottom collection plate 24 near the front of the workstation. Then successive washings can be carried out at each of the two center vacuum chambers whereat open-bottom collection plates are placed. Next, a final collection of filtrate can take place at the vacuum chamber near the rear of the workstation, whereat another closed-bottom collection tray is located.

With regard to spatial orientation, it should be noted at this point that the various components (e.g., upper chamber, mini-column plate, filter element, drip-director plate, frame, cross-flow restrictor, collection-well plate, and lower chamber) are illustrated and described herein as being stacked in vertical relationship, with the upper vacuum chamber being the topmost component. Further, each microfiltration well is described as having a central axis disposed in a substantially vertical fashion, with a flow pathway extending downwardly through the well. It should be noted, however, that these orientations have been adopted merely for convenience in setting forth the detailed description, and to facilitate an understanding of the invention. In practice, the invention contemplates that the components and wells may be disposed in any orientation.

In another of its aspects, the present invention provides for the covering and sealing of multi-well trays containing fluid samples:

In one embodiment, shown in FIGS. 11 through 14, a cover member, indicated generally by the reference numeral 150, includes an upper shell portion, denoted generally as 154, supporting a sealing layer or undersurface, indicated generally as 156 (FIG. 11), on its lower face. Upper shell portion 154 is comprised of a substantially planar expanse 158 (FIGS. 12 and 13) and a depending circumferential sidewall 160 laterally surrounding undersurface 156. Along the length and width dimensions, undersurface 156 is configured with generally the same geometry as the upper surface of multi-well plate 24, permitting it to cover the entire array of well openings 26a.

Figure 11:
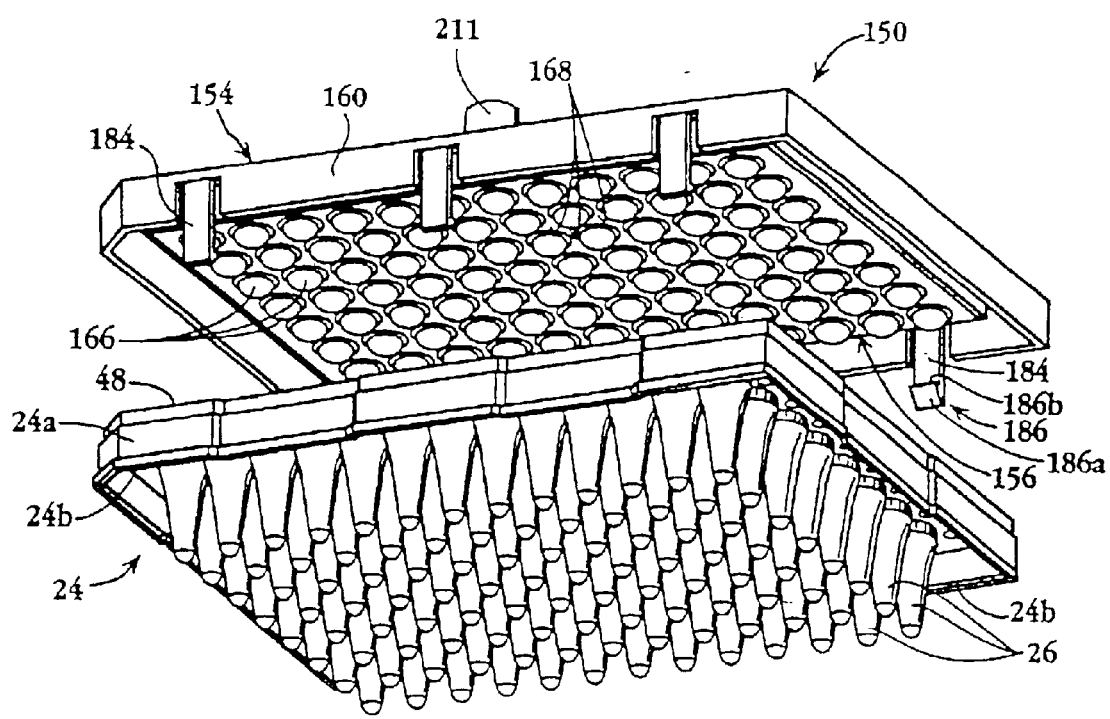
FIG. 11 is a perspective view of a cover member, having an array of resiliently flexible half-dome features on its lower face, disposed over a multi-well tray, in accordance with an embodiment of the present invention.

As best seen in FIG. 11, undersurface includes a plurality of individual nodules, such as 166, arranged in a rectangular array corresponding to the array of wells 26 of collection tray 24. Each of the nodules 166 preferably has a downwardly convex, e.g., dome-shaped, lower portion, though other shapes may be used. The nodules 166 are made of a resiliently flexible material held in a predetermined, spaced relationship from each other by a web or sheet 168. Web 168 may be integrally formed with nodules 166, as shown, or it may be formed separately, with the nodules molded or adhesively attached to the web at appropriate locations.

Cover 150 is preferably comprised of a substantially rigid material that, when pressed down at opposing peripheral edge regions against corresponding regions of ridge 48 along the periphery of multi-well plate 24, can maintain an annular region of each nodule 166 in pressing engagement with an upper lip 26b of a respective well 26. To evenly distribute the downward force across undersurface 156, integral beams, such as 172 and 174, can extend laterally and/or longitudinally across the top surface of upper shell portion 154, providing increased rigidity.

Undersurface 156 is formed of a resiliently deformable material that, when compressed over openings 26a, is capable of forming a seal. Suitable materials for forming undersurface 156 include, for example, synthetic rubber-like polymers such as silicone, sodium polysulfide, polychloroprene (neoprene), butadiene-styrene copolymers, and the like. Upper shell portion 154 is formed of a substantially rigid material such as nylon, polycarbonate, polypropylene, and the like.

In one preferred embodiment, the cover of the invention is made by an injection co-molding process wherein an upper shell portion is first molded, and then a sealing undersurface is injection molded to the shell portion. A preferred nylon material useful for forming the upper shell is available commercially as ZYTEL® grade 101 (DuPont Co., Wilmington, Del.). To avoid heat-induced damage to the molded nylon shell portion, preferred silicone materials have relatively low injection and curing temperatures (e.g., less than about 180° C.). One particularly preferred silicone material useful for co-molding the undersurface is available commercially as COMPU LSR 2630 clear (Bayer A G, Germany).

To secure undersurface 156 to upper shell portion 154, a series of holes (not shown) are formed through the shell's planar expanse 158. Upon injecting a liquid silicone from the bottom side of the upper shell portion 154, the silicone penetrates the holes and forms nodules, such as 180, having a greater diameter than that of the holes, adjacent the topside of the upper shell portion 154. Upon curing, the silicone contracts slightly, pulling the nodules 180 and the expansive undersurface 156 toward one another. In this way, a snug attachment is effected at several locations holding the undersurface 156 against the lower face of the upper shell portion 154.

Figure 13:
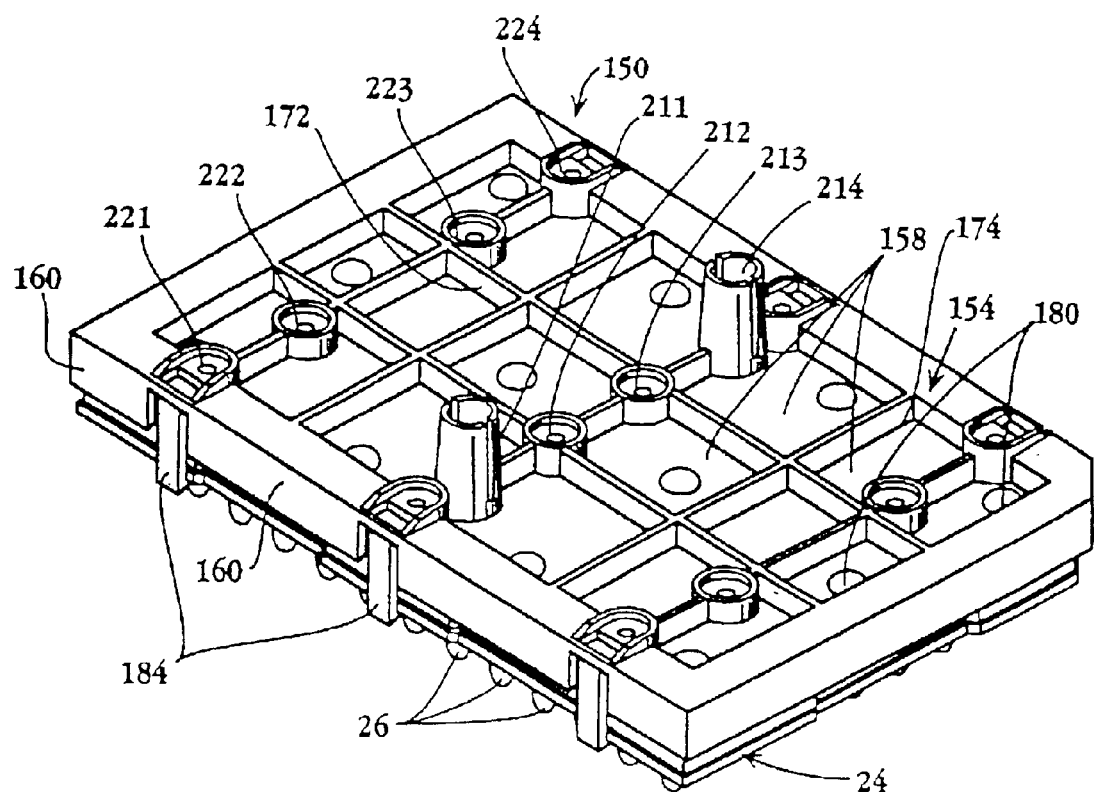
FIG. 13 is a perspective view showing the cover of FIGS. 11 and 12 disposed over the openings of a multi-well tray and releasably snap-locked to the multi-well tray, according to an embodiment of the invention.
Figure 14A:
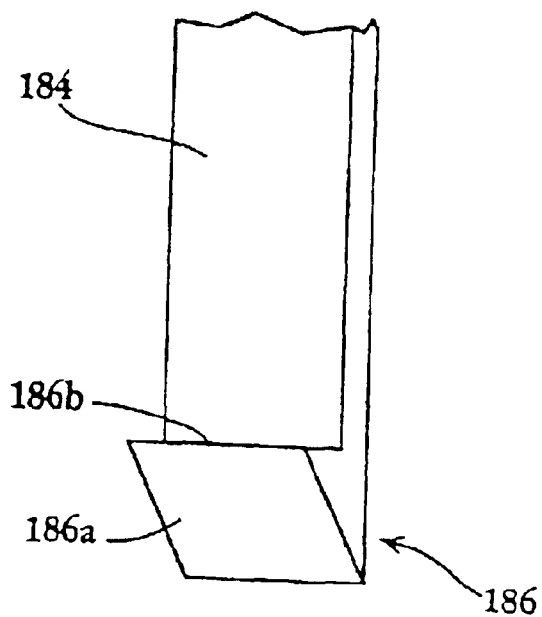
FIGS. 14(A) and 14(B) are enlarged, perspective and side-sectional views, respectively, showing a releasable snap-locking assembly for securing a cover of the invention to a multi-well tray, according to an embodiment of the present invention.
Figure 14B:
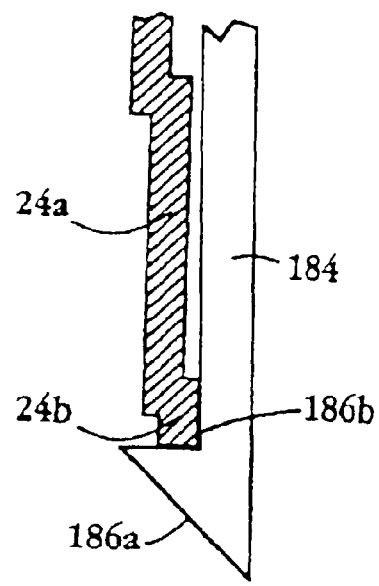

Cover 150 is secured to multi-well tray 24 by a releasable attachment means. In the embodiment of FIGS. 11–14, the attachment means includes a plurality of integrally formed, resiliently deflectable arms, such as 184, depending from opposing lateral sides of upper shell portion 154. At an end distal from upper shell portion 154, each arm 184 is provided with a catch or hook 186 adapted to hold on to a circumferential sidewall 24a formed about multi-well plate 24. As best seen in FIGS. 11 and 14, each catch 186 is substantially formed in the shape of a half-arrow, having (i) a downwardly and outwardly angled cam surface 186a, and (ii) an upper shoulder or stop portion 186b. Upon moving the cover 150 toward a seated position over the well openings 26a, the cam surface 186a of each catch 186 slides down over the circumferential sidewall 24a of collection plate 24, thereby defecting arms 184 laterally outward. Once the shoulder 186b of each catch 186 clears the lower edge 24b of circumferential sidewall 24a, arms 184 snap inward, locking the cover 154 in a closed position, as shown in FIG. 13.

To release the snap-locked cover 154 from multi-well tray 24, arms 184 can be pulled outwardly, away from circumferential sidewall 24a, so that each shoulder 186b clears lower edge 24b. Cover 154 can then be separated from the tray 24 to reveal the well openings 26a.

Figure 15:
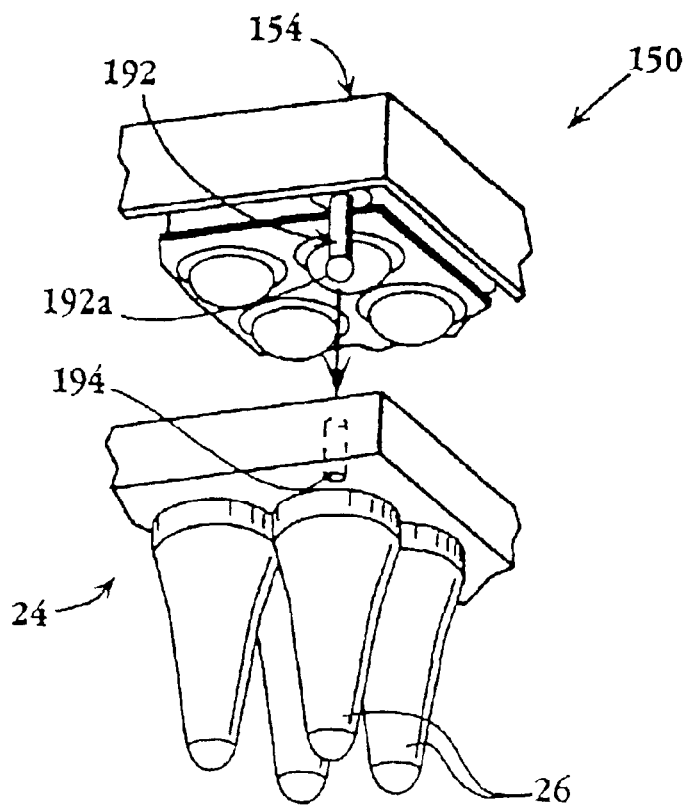
FIG. 15 is a perspective view showing an assembly for releasably securing a cover of the invention to a multi-well tray, according to a further embodiment of the invention.

In an alternative embodiment, shown in FIG. 15, the releasable attachment means includes a plurality of nubs or protrusions 192 having resiliently deformable terminal bulbs 192a depending at various points along the periphery of the lower surface of cover 154. In this embodiment, nubs 192 are receivable within complementary bores 194 formed along corresponding regions of the upper surface of multi-well plate 24. Frictional engagement of each bulb 192a with an inner sidewall of a respective bore 194 holds the cover 154 in place over the multi-well plate 24.

Figure 12:
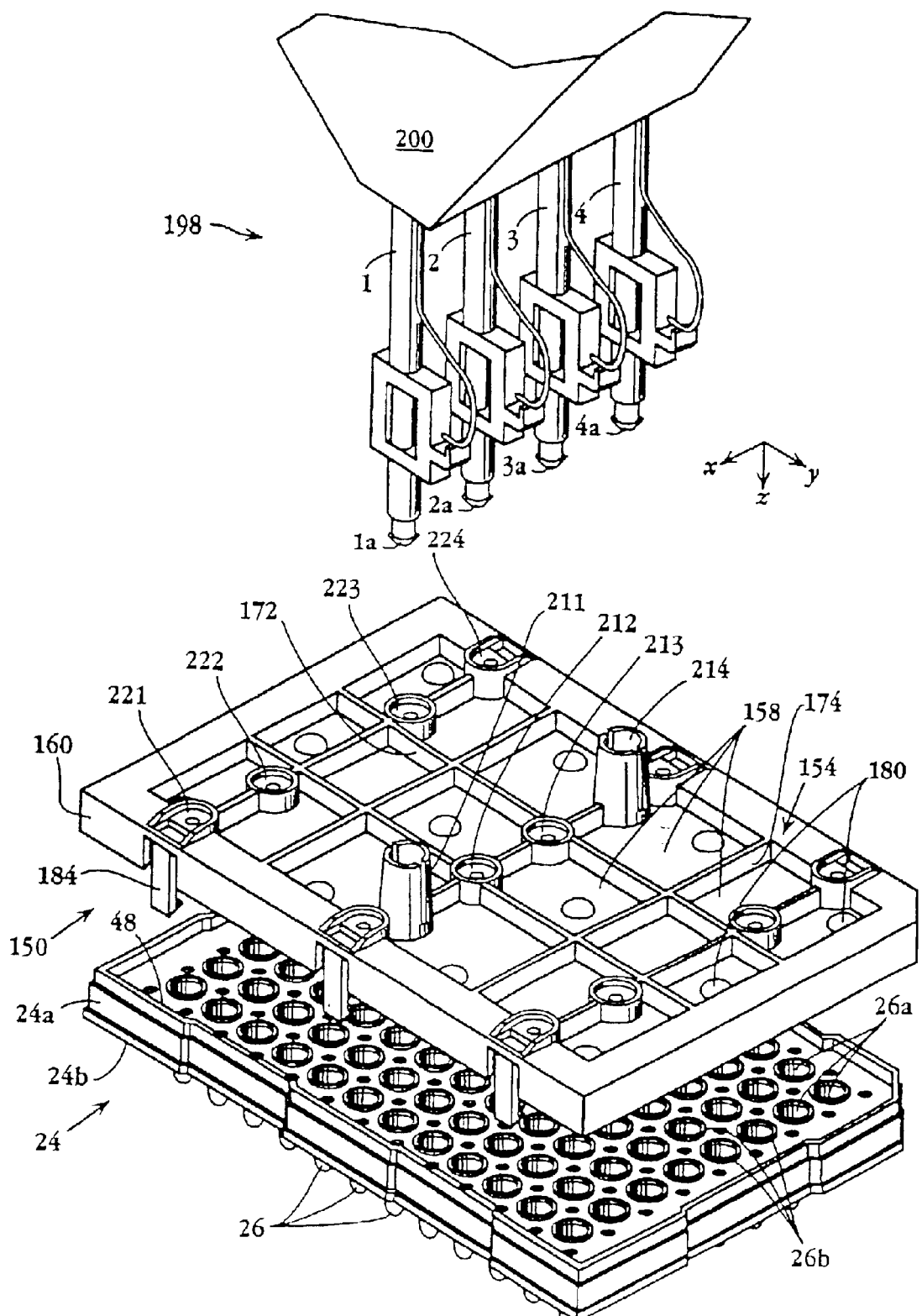
FIG. 12 is another perspective view of the cover member of FIG. 12, showing a plurality of sites on the cover's upper surface for receiving the lower end regions of elongated, fluid-handling fingers of a fluid-handling robot positioned above the tray, in accordance with an embodiment of the present invention.

In one preferred embodiment, best seen in FIG. 12, structure is provided along the top of upper shell portion 154 that facilitates automated handling using a robotic fluid-handling apparatus. An exemplary robotic system is available commercially under the tradename TECAN® RSP (Tecan A G; Hombrechtikon, Switzerland). In the illustrated arrangement, the robotic system, denoted generally as 198, includes four elongated aspiration and injection fingers, denoted as 14, mounted on a robotic arm 200 at respective points generally defining a line. Arm 200 can translocate fingers in the x/y direction along a generally horizontal plane, throughout which the longitudinal axes of fingers 1–4 are maintained in fixed, spaced relation to each other. The longitudinal axes of fingers 14 are evenly spaced from about 9 mm to about 36 mm, and preferably about 18 mm, apart from one another. Each of the fingers 14 can be separately translocated in the z direction along a respective, generally vertical axis. Movement of arm 200 and fingers 1–4 is preferably carried out under the control of a programmed computer (not shown) by known techniques.

The TECAN® RSP can be used, in a known manner, to transfer fluids to and from various chambers, e.g., wells of a microplate 24, vials 206, troughs 208 and the like, disposed on a working surface, such as the worktable 202 shown in FIG. 16. Other known uses for the TECAN® RSP include, for example, reagent addition, dilution, and mixing.

As previously mentioned, the present invention provides structure along the top of upper shell portion 154 that facilitates automated handling. Advantageously, such structure expands the capability of the robotic system 198 beyond conventional fluid-handling tasks to include novel tasks such as picking up covers, placing covers over multi-well plates, and securing the covers to the plates, as described below. As shown in the embodiment of FIG. 12, such structure can include longitudinally slotted, resiliently expandable sleeve-like members, such as 211 and 214, each adapted to receive the tip region of one of the fingers 1–4 such that the finger becomes wedged therein. Such structure further includes a plurality of landing seats, e.g., 221–224 and 212–213, defined by rimmed depressions or bores having a diameter wider than that of fingertips (1a–4a), providing strategic regions whereat the fingers can abut the upper surface of the cover with a reduced risk of slippage.

Generally, frictional engagement of each sleeve 211, 214 with one of fingertips 1a–4a permits the robot to pick up, carry and/or place cover 150, as desired. Once suitably placed, the cover can be released by extending one or more free fingers against corresponding landing seats on the upper surface of the cover, while retracting the wedged fingertips. In an exemplary operation, fingers 1, 4 are extended downward in the z direction toward a cover 150 disposed, for example, on a surface of a workstation 202 so that fingertips 1a, 4a enter and become wedged within respective expandable sleeves 211, 214. Fingers 1, 4 are then partially retracted in the z direction, in unison, to lift cover 150 above the working surface. Next, the lifted cover 150 is translocated by moving arm 200 along the x/y direction to another area of the working surface. Fingers 1, 4 are then extended downward, in unison, in the z direction to lower cover 150 onto a multi-well tray 24 containing, for example, a plurality of separately collected fluid samples. Cover 150 is released from the robot 198 by extending free fingers 2, 3 downward against landing seats 212, 213 on the upper surface of cover 150, and retracting fingers 1, 4 from sleeves 211, 214. Finally, all of the fingers (1–4) are raised toward arm 200 to a fully retracted position.

Employing a releasable attachment means, cover 150, so placed, can be snap-locked to the multi-well tray 24 by applying a downward force from above. In an exemplary operation, fingers 1, 4 are extended downward in the z direction to abut landing seats 221 and 223, respectively, on the top of cover 150. The downward motion of finger 1 is continued against landing seat 221 so that the locking arm 184 thereunder is moved into snapping engagement with circumferential sidewall 24a of multi-well tray 24. In the meanwhile, finger 4 is held substantially motionless adjacent landing seat 223 in order to oppose any tendency of the cover to flip up. An appropriate downward force is then applied at landing seats over the remaining arms until all of the arms are snap-locked to the multi-well tray.

While it should be understood that the covers described herein can be employed in a wide variety of situations, they are particularly useful for protecting a plurality of fluid samples separately contained in an array of closed-bottom collection wells against evaporation and/or cross-contamination during long-term storage. For example, fluid filtrate (e.g., containing purified or concentrated nucleic acids, such as RNA or DNA) can be collected using the microfiltration apparatus of FIGS. 1 to 3. The collection wells can then be sealed by snap-locking the cover 150 of FIGS. 11–14 thereto, using a TECAN® RSP fluid-handling robot as just described. The covered multi-well tray can then be placed in a freezer for storage. The covers can be reused multiple times, if desired.

By utilizing a single robotic fluid-handling arm to carry out a variety of tasks at the workstation, valuable working space is conserved. Moreover, equipment and programming expenses are avoided by obviating the need for additional robotic devices, e.g., grippers, for picking up, moving, placing and securing covers.

The present invention also provides for the sealing of multi-well trays with heat-seatable covers. Generally, the heat-sealing apparatus of the invention includes a pick-and-place assembly adapted to lift an individual, precut, heat-sealable sheet or film from a bin and place the sheet over a plurality of well openings of a multi-well tray. A heatable platen is provided for engaging the sheet, so placed, and heat sealing the sheet to the upper surface of the multi-well plate, thereby forming a seal over each well. Advantageously, the operation is carried out in an automated fashion.

According to one embodiment, shown in FIGS. 16–24, a first, substantially planar work surface, generally denoted as 302, is positioned over a cooler, indicated generally by the reference numeral 306. A plurality of rectangular cavities, such as cavities 310, are formed through the work surface, each adapted to support a multi-well tray therein, such as tray 324, with the lower side of the tray disposed in communication with the temperature-controlled environment of cooler 306. In a preferred embodiment, four such cavities are formed through work surface 302. When a multi-well tray is properly positioned in one of cavities 310, an outer circumferential edge or lip of the tray rests on a region of the surface circumscribing the cavity, with the bottom regions of the wells extending below the surface into the cooler. Cooler 306 is adapted to maintain the samples at a desired, reduced temperature (e.g., about 4° C. for fluid samples containing purified or concentrated nucleic acids, such as RNA).

Means are provided to ensure proper placement (i.e., orientation) of a multi-well tray in a respective cavity. According to one embodiment, one face of a triangular key feature, indicated as 322, is rigidly attached to the work surface 302 proximate a corner of each cavity 310. Further, one corner of each multi-well tray is angled, as at 324d, to sit on work surface 302 closely adjacent the edge of key 322 facing the cavity 310, when the tray is properly (fully) seated. It should be appreciated that only the angled corner 324d of tray 324 can sit on work surface 302 adjacent key feature 322. If tray 324 is placed in the cavity in the wrong orientation, a non-angled corner of tray 324 (i.e., one other than 324d) will land on the upper face of key 322, thereby prohibiting proper (full) seating of tray 324 in manner that will be apparent to an operator.

A second, substantially planar working surface, denoted as 332, is positioned alongside first surface 302, such that the two surfaces are substantially coplanar. A bin or tray, indicated as 336, for holding individual sheets of heat-sealable covers is held in a frame, denoted generally as 338, affixed near one end of second working surface 332. Tray 336 is adapted to hold a plurality of heat-sealable sheets, denoted generally as 342, vertically stacked face-to-face, such that the topmost sheet is always presented for retrieval by a suction picker assembly, denoted as 394, at substantially the same, predetermined vertical height. For example, tray 336 can rest on a spring-biased bed (not shown) adapted for vertical motion within frame 338.

Figure 18:
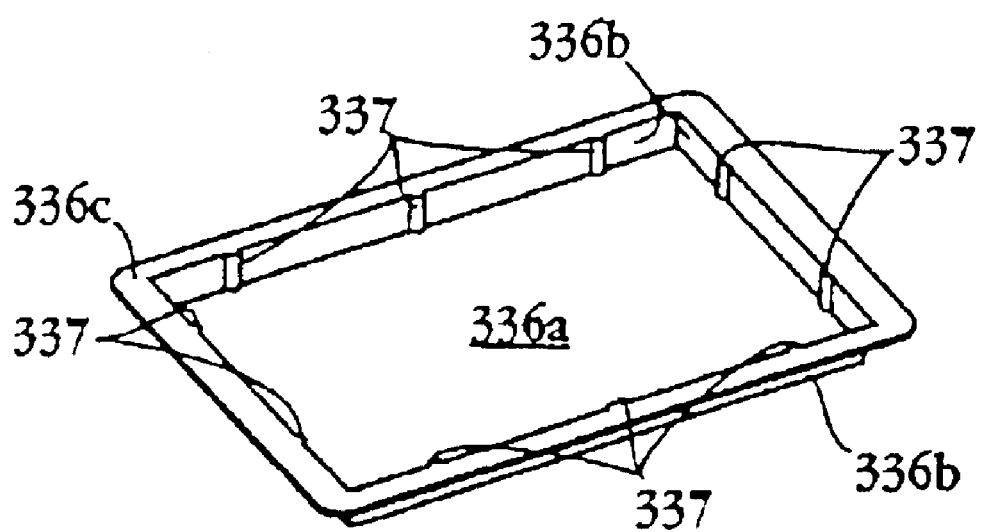
FIG. 18 is a perspective view showing a tray or bin for holding a stack of heat-sealable sheets, constructed in accordance with an embodiment of the present invention.

Tray 336 is preferably formed as an integral unit using a conventional thermoforming process. In one embodiment, tray 336 is formed of a lightweight plastic material, such as PETG, or other suitable thermoplastic resinous material. As best seen in FIG. 18, tray 336 is formed with a bottom 336a, four sidewalls 336b, an outwardly extending circumferential lip 336c, and an open top. As is well known in the art of thermoforming, it is generally necessary to provide a draft for the sidewalls of a thermoformed tray. Draft is the slight taper provided in a design of a thermoformed part that permits the part to be removed from the mold, after curing, without disturbing the part's walls. In the thermoformed tray of the present invention, the distance between opposing sidewalls of the tray slightly increases along the direction from the bottom of the tray to the top of the tray. For example, the sidewalls can be provided with a lift-out slope in the range of about 1–10 degrees. In one embodiment, the lift-out slope is about 5 degrees.

As a consequence of the draft, the planar area bounded by the tray's sidewalls 336b, parallel to the tray's bottom 336a, gets progressively larger moving along a direction from the bottom 336a to the top of the tray. To prevent shifting of the sheets (not shown in FIG. 18) held within the tray, particularly at the wider, upper regions thereof, ribs, such as 337, are provided along each sidewall 336b. Ribs 337 are configured to provide a substantially straight surface or edge for continuously contacting a point, and preferably plural points, on each peripheral side-edge of each sheet of a stack, throughout each sheet's range of vertical motion. Thus, ribs 337 serve to guide each sheet as it is moved vertically through tray 336, and to ensure that each sheet is maintained in a desired orientation within the tray 336. In the illustrated embodiment, ribs 337 are provided as integrally molded, opposing pairs extending along opposing sidewalls of the tray. The ribs running along each sidewall 336b are sufficiently spaced apart so as to prevent the sheets held in the tray from becoming skewed. In this embodiment, each rib 337 provides a vertically extending, elongated line or surface that is substantially normal to a plane defined by the bottom 336a of tray 336. Due to the upwardly divergent nature of the tray's sidewalls 336b, the ribs 337 become slightly more pronounced (i.e., they extend further outward from each sidewall's major surface) along the direction from the bottom 336a of tray 336 to the top of tray 336.

Figure 17:
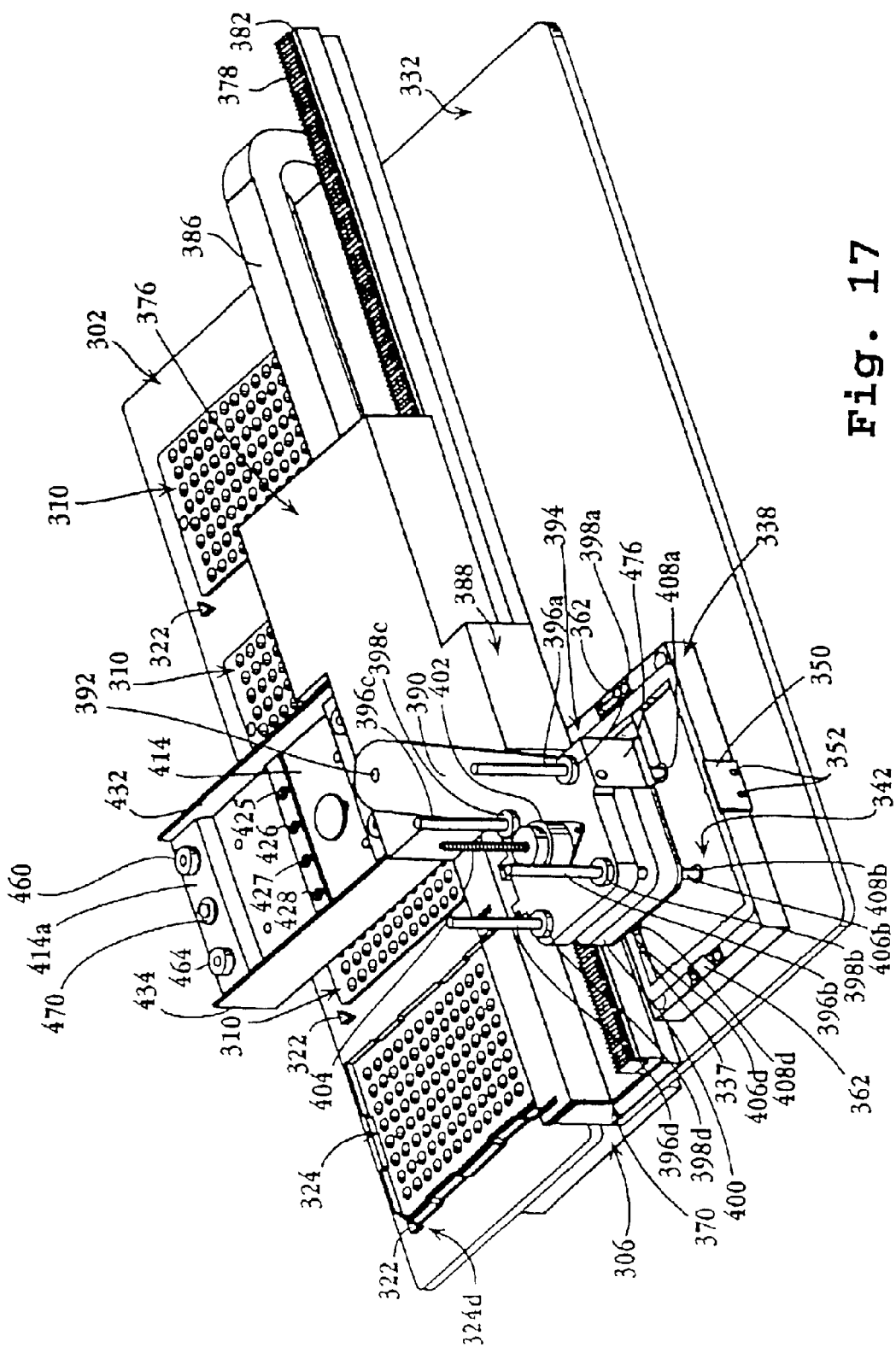
FIG. 17 is a perspective view of an automated station for applying heat-sealable sheets over the wells of a multi-well tray, in accordance with an embodiment of the present invention.
Figure 19A:
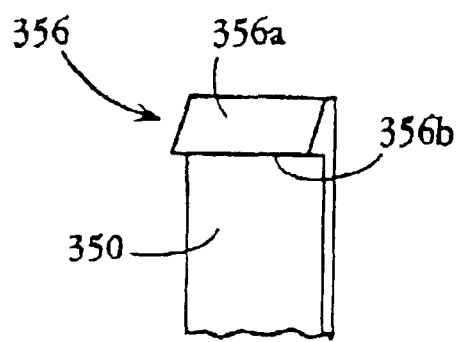
FIGS. 19(A) and 19(B) are enlarged, perspective and side-sectional views, respectively, showing a releasable snap-locking assembly for securing a tray or bin, such as shown in FIG. 18, to a frame assembly situated, for example, at a heat-sealing station such as shown in FIG. 17, in accordance with one embodiment of the present invention.
Figure 19B:
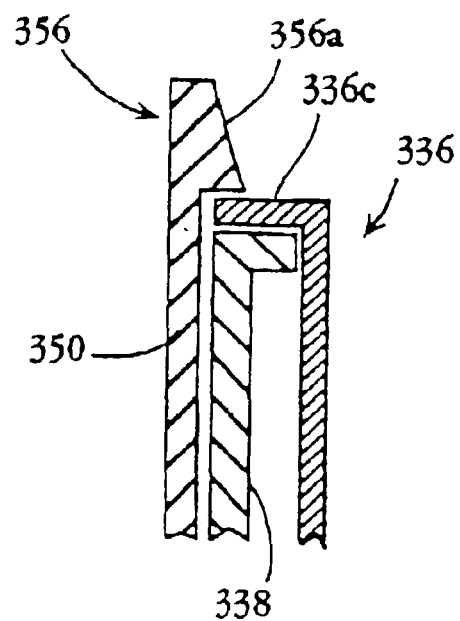
Figure 20:
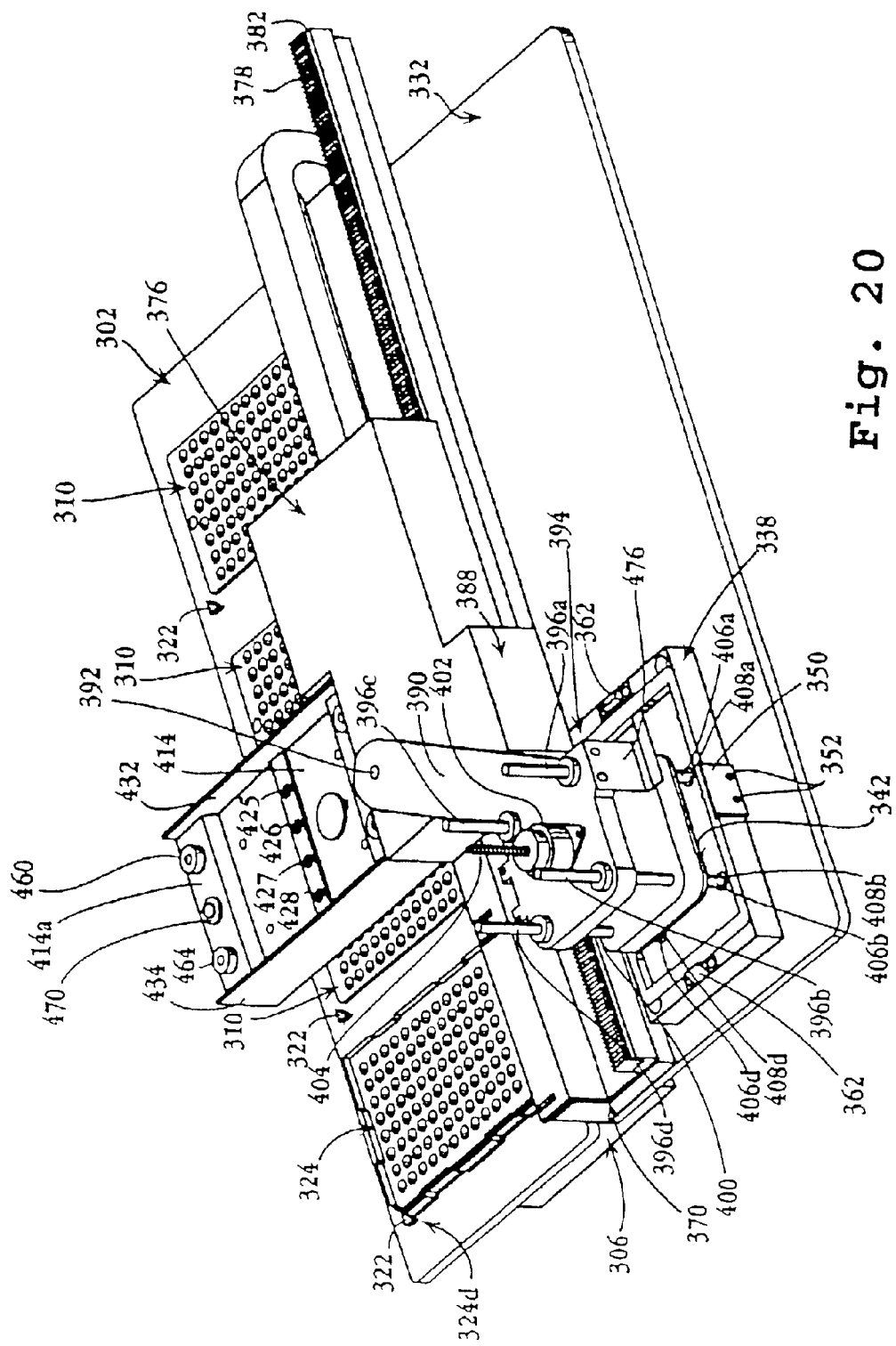
FIGS. 20 to 23 are perspective views illustrating various features, as well as the operation of, the automated heat-sealing station of FIG. 17, according to an embodiment of the present invention.

A releasable attachment means is provided to prevent inadvertent removal of tray 336 from frame 338. In one embodiment, the attachment means includes resiliently deflectable arms, such as 350, extending upwardly from opposing lateral sides of frame 338. Each arm 350 is rigidly attached near its lower end, e.g., by way of fasteners 352, to a lower region of frame 338 proximate work surface 332. As best seen in FIGS. 19(A)–19(B), the upper region of each arm 350 is provided with a catch or nook 356 adapted to hold on to the circumferential lip 336c at the top of tray 336 when the tray is disposed in a fully seated position. Each catch 350 is substantially formed in the shape of a half-arrow, having (i) an upwardly and outwardly angled cam surface 356a, and (ii) a lower shoulder or stop portion 356b. Upon moving tray 336 toward a seated position within frame 338, the cam surface 356a of each catch 356 slides over the outer peripheral edge of lip 336c, thereby deflecting each arm 350 laterally outward. Once the lip passes below shoulder 356b, the arms snap inward, locking the tray in the frame, as shown in FIG. 17.

To release the snap-locked tray 336 from frame 338, arms 350 can be bent outwardly, apart from one another, so that each shoulder 356b clears the outer edge of lip 336c. Tray 336 can then be lifted out of frame 338.

An abutment, denoted as 362, is rigidly secured on the upper surface of frame 338 near each longitudinal end. Abutments 362 provide substantially vertical, confronting surfaces that guide tray 336 as it is being placed in frame 338, and that maintain the tray in a desired position while it is seated.

Sheets 342 may be made of any substantially chemically inert material that can form a seal with the upper surface of a multi-well tray, or appropriate regions thereof (e.g., an upstanding rim or lip about the opening of each well), when applied with moderate heat (e.g., 90–170° C.) under moderate pressure (e.g., about 10–35 lbs.). For example, sheets 342 may be formed of a polymeric film, such as a polystyrene, polyester, polypropylene and/or polyethylene film. Suitable polymeric sheets are available commercially, for example, from Polyfiltronics, Inc. (Rockland, Mass.) and Advanced Biotechnologies (Epsom, Surrey England UK). In one embodiment, each sheet is a substantially clear polymeric film, about 0.05 millimeters thick, that permits optical measurement of reactions taking place in the wells of tray 324. For example, the present invention contemplates real time fluorescence-based measurements of nucleic acid amplification products (such as PCR) as described, for example, in PCT Publication WO 95/30139 and U.S. patent application Ser. No. 08/235,411, each of which is expressly incorporated herein by reference. Generally, an excitation beam is directed through a sealing cover sheet into each of a plurality of fluorescent mixtures separately contained in an array of reaction wells, wherein the beam has appropriate energy to excite the fluorescent centers in each mixture. Measurement of the fluorescence intensity indicates, in real time, the progress of each reaction. For purposes of permitting such real time monitoring, each sheet in this embodiment is formed of a heat-sealable material that is transparent, or at least transparent at the excitation and measurement wavelength(s). A preferred heat-sealable sheet, in this regard, is a co-laminate of polypropylene and polyethylene.

Often, heat-sealable films or sheets are obtained as a web in the form of a roll. Not surprisingly, such rolls are often bulky and heavy. Moreover, the equipment required to properly cut them into a desired shape can be costly and space consuming, as well. Advantageously, the heat-sealable sheets provided by the present invention are pre-cut to appropriate dimensions, and stacked to inside tray. As contemplated herein, a tray, such as 336, holding a stack of sheets 342 is packaged as a pre-assembled unit, which is readily opened and inserted into frame 338.

A linear track 370, supporting a carriage assembly 376, is mounted longitudinally across work surface 332, adjacent to cooler 306. A reversible drive means is adapted to move carriage 376 back and forth along track 370, as desired. In the illustrated embodiment, the drive means includes a nylon rail 382 having upwardly facing teeth 378 formed along its top surface, from one end to the other. Teeth 378 are adapted to mesh with a circular, eternally-toothed, motor-driven gear (not shown) disposed for rotation inside the carriage housing. A flexible guide or conduit 386, as can be obtained commercially from KabelSchlepp America, Inc. (Milwaukee, Wis.), is disposed alongside rail 382 for containing various cables and wires (not shown) of the apparatus.

Figure 21:
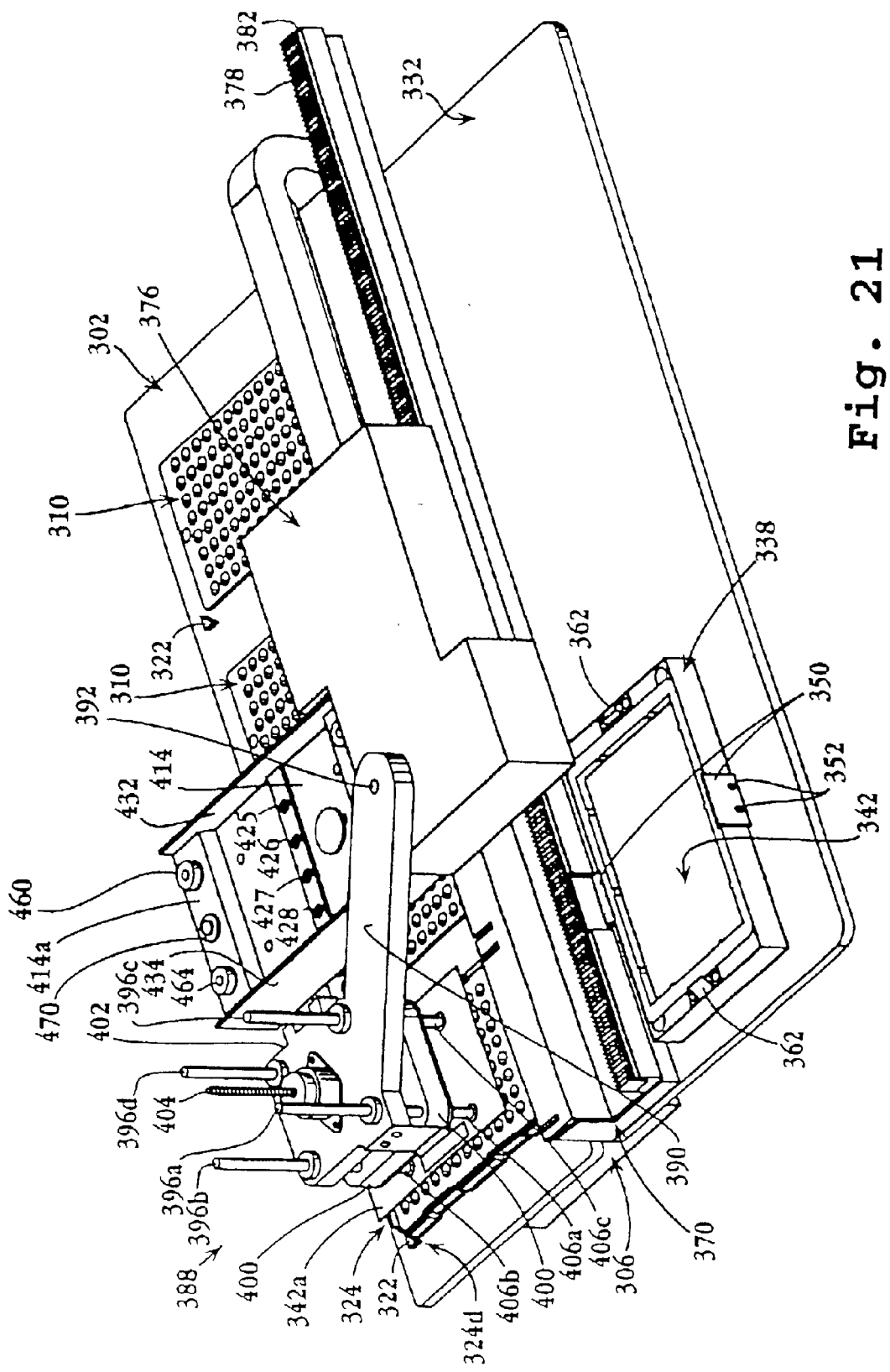
Figure 22:
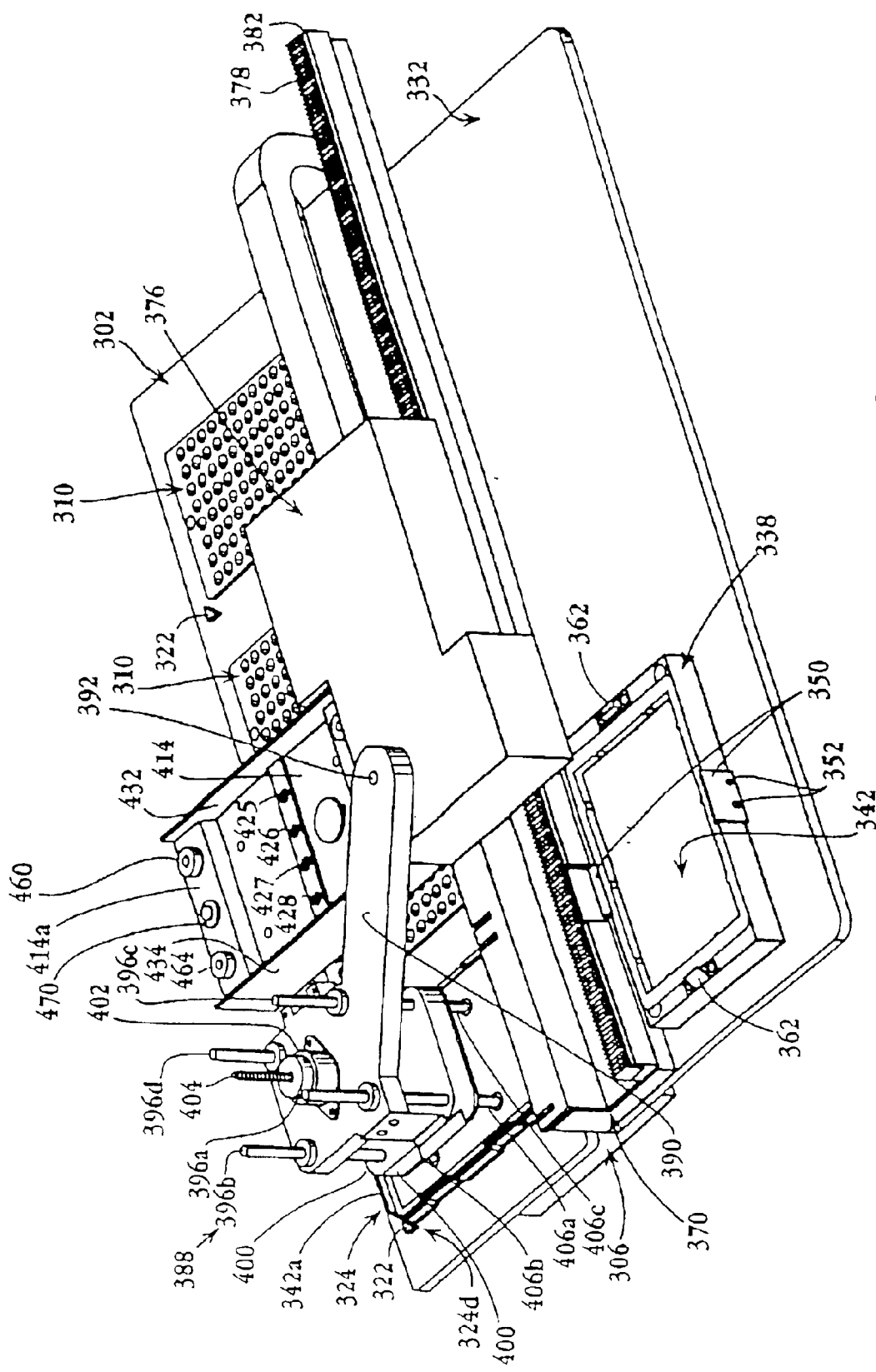
Figure 23:
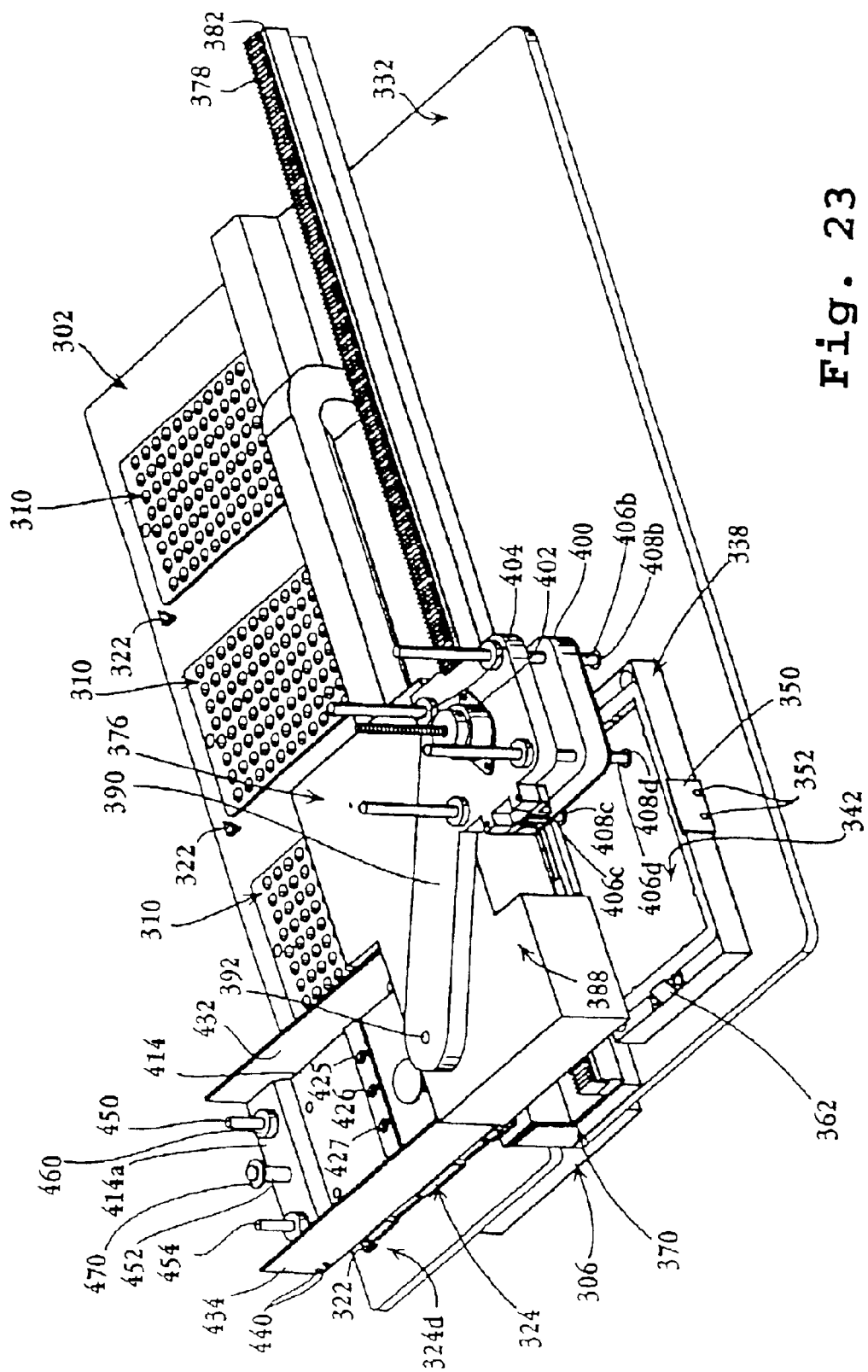

Carriage 376 supports a pick-and-place assembly, indicated generally by the reference numeral 388, and a heatable platen assembly, denoted as 412. Pick-and-place assembly 388 includes an elongated picker arm 390 supported above the carriage via a rotatable mount 392 extending through an upper surface of carriage 376. The rotatable mount can be, for example, a driven shaft coupled to a reversible stepper motor (not shown) held within the carriage housing. Arm 390 is attached to driven shaft 392 so as to rotate therewith. Arm 390 is adapted for movement along a generally horizontal plane between a "home" position (FIGS. 16 and 23), a "pick-up" position (FIGS. 17 and 20), and a "drop-off" position (FIGS. 21 and 22).

The other end of arm 390 supports a suction picker assembly, indicated generally by the reference numeral 394, adapted to pick up a heat-sealable sheet from stack 342 held in tray 336, and to place the sheet over a multi-well tray held in one of the cavities at cooler 306. Suction picker assembly 394 includes four elongated guide rods, denoted as 396a–396d, each supported for reciprocal sliding movement within a respective linear bearing 398a–398d held in a bore (not shown) extending vertically through arm 390. Rods 396a–396d are secured, to at their lower ends, to the top of a plenum, denoted as 400.

Plenum 400 can be moved up and down to a desired vertical height by way of a linear motion means. The linear motion means can be a stepper motor, such as 402, mounted on arm centrally of rods 396a–396d. Rotational motion of stepper motor 402 causes a lead screw 404, passing centrally through motor 402, to move up or down along its longitudinal axis, dependent upon the direction of rotation. The lower end of lead screw 404, in turn, is rotatably journaled to plenum 400. Thus, upon stepping motor 402, plenum 400 will move up or down with linear movement of lead screw 404.

A plurality of suction legs, such as 406a–406d, depend from a lower side of plenum 400. In the illustrated embodiment, one such leg is disposed near each corner of plenum 400. A downwardly facing suction cup, such as 408a–408d, is attached at the lower end of each leg 406a–406d. The face region of each suction cup 408a–408d is disposed in fluid communication with plenum 400 via a channel (not shown) extending longitudinally through a respective leg 406a–406d. Plenum 400, in turn, communicates with a remote vacuum source (not shown) via a suitable hose. Upon evacuating plenum 400, a vacuum is established at the face region of each suction cup 408a–408d.

Figure 24:
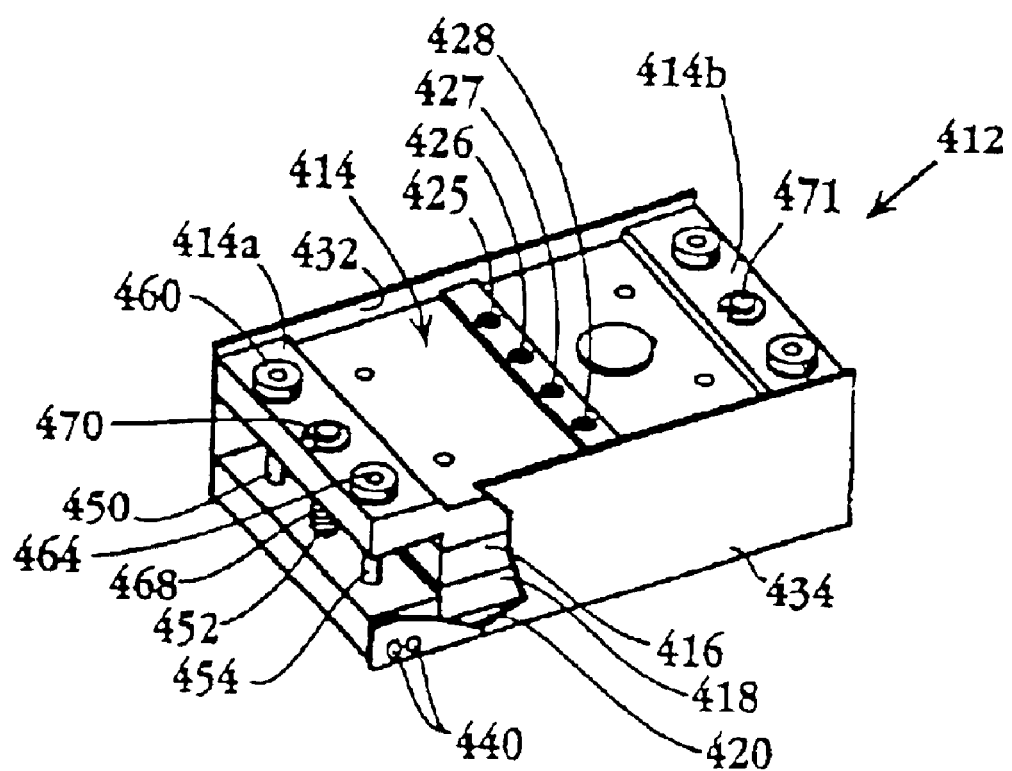
FIG. 24 is a perspective view, with portions broken away, of a heatable platen assembly as used, for example, in the heat-sealing station of FIGS. 17 and 20–23, according to an embodiment of the present invention.

With additional reference to FIG. 24, platen 412 is a multi-layered assembly, including (from top to bottom) (i) a support plate 414; (ii) a heat-insulating layer 416, (iii) a heater 418; and (iv) a thermally conductive, conformable pad 420; each of which is described more fully below.

Support plate 414 is formed of a rigid material that, when pressed down from above, is capable of transmitting the downward pressure across the various underlayers 416, 418, 420, so that the lower surface of the thermally conductive, conformable pad 420 is pressed against the upper surface of a multi-well tray. Suitable materials for forming support plate 414 include metals, such as aluminum and the like. A plurality of depressions or indentations, such as 425–428, are provided along the upper surface of plate 414, providing landing sites, or seats, for the fingers of a fluid-handling robot, such as a four-fingered TECAN® RSP, to abut and press down upon the platen 412, as described below.

The heat-insulating layer 416 thermally isolates the upper support plate 414, and associated elements, from heat and hot components thereunder. In one preferred embodiment, the heat-insulating material is a phenolic block.

The heater 418 is preferably an electrically resistive heating element (not shown) disposed within a heat-conductive metallic plate, such as an aluminum plate or the like. The heating element can be, for example, a silicone rubber heater. A preferred silicone rubber heater (80 Watts, 24 Volts) is available commercially from Micro Products, Inc. (Minneapolis, Minn.).

The thermally conductive, conformable pad 420 acts as a thermal interface between the heated metallic plate and the area along the upper surface of a multi-well plate. A preferred material for forming the pad is available commercially under the trade name Gap Pad™ from The Bergquist Company; (Edina, Minn.). Gap Pad™ is a highly conformable silicone polymer filled with alumina (See, e.g., U.S. Pat. No. 5,679,457; expressly incorporated herein by reference). The pad, attached to the underside of the heated metallic plate, has a thickness of about 0.10" to 0.20", and preferably about 0.160". The pad provides a heated surface capable of conforming to the contours of the upper surface of the multi-well plate for applying a heat-sealable sheet thereto.

Platen 412 further includes a frame structure having two substantially vertical side panels 432, 434 held in fixed spaced relation by a pair of rectangular crossbar members, such as crossbar 438. The crossbar members are rigidly attached to the side panels 432, 434, e.g., by way of fasteners 440, so as to form narrow, flat floor regions bridging the confronting faces of the side panels 432, 434, at each longitudinal end thereof (only one of which is visible in the figures). In an alternative embodiment, the frame structure is cast as a unitary piece.

Each end of support plate 414 has an overhang region, such as 414a and 414b, that projects longitudinally beyond the various underlayers 416, 418, 420. Each overhang region 414a, 414b is about the same size, along its length and width dimensions, as one of the crossbar members. As best seen in FIG. 24, the lower surface of overhang region 414a faces the upper surface of a crossbar member 438. Although not visible in the figures, it should be noted that the same arrangement exists on the opposing side of the frame structure.

Three elongated, cylindrical rods are disposed substantially normal to an upper, flat surface of each crossbar member, at spaced points generally defining a line. For example, FIG. 24 shows rods 450, 452, 454 near one end of platen 412. Similar structure exists near the other end of platen 412, as well. The lower end of each rod is rigidly attached to its respective crossbar member, while the upper (free) end is passed through a respective bore (not shown) formed vertically through a respective overhang region, 414a or 414b. The two outer rods on each crossbar member, such as rods 450 and 454, are received in linear bearings, such as bearings 460 and 464, held within such bores, and serve to guide the platen 412 as it moves up and down along a generally vertical direction. The center rod on each crossbar member, such as rod 452, forms a part of a biasing means that acts to urge the platen 412 upward. In this regard, a compression spring, such as spring 468, is concentrically mounted about the center rod at each end of platen 412, with the spring pre-compressed between the upper surface of its respective crossbar member and the lower surface of a confronting overhang region, 414a or 414b. In its desire to extend, the spring provides a continuous, upwardly-directed force that, in the absence of an equal or greater opposing force, is sufficient to position platen 412 in a fully raised position, whereat the support plate 414 is disposed proximate the top edge regions of side panels 432, 434.

An E-style retaining ring, such as 470 and 471, is mounted near the top of each center (spring-bearing) rod, limiting the upward movement of the support plate 414. In an alternative embodiment (not shown), the upper edge of each side panel can be angled inward, e.g., 90 degrees relative to the major surface of the panel, to form a lip that acts to limit the upward movement of the support plate.

As previously indicated, pick-and-place assembly 388 is used to pick up individual heat-sealable covers from a holding tray 336 and place them on a multi-well tray 324. The heatable platen 412 applies the heat and force necessary for effecting a proper seal.

In an exemplary operation, and with reference to FIGS. 16–24, the heat sealing station apparatus begins the sealing process by rotating picker arm 390 from the home position (FIGS. 16 and 23) to the pick-up position (FIGS. 17 and 20), through an arc of about 90°. Carriage 376 moves along linear track 370, as necessary, until suction picker assembly 394 is positioned directly above a tray 336 holding a stack of polyethylene/polypropylene covers 342. Here, suction picker assembly 394 is driven down, by way of stepper motor 402 and lead screw 404, until each suction cup 408a–408d contacts the uppermost sheet of stack 342. Plenum 400 is then evacuated by a remote vacuum source (not shown) in order to establish a vacuum, e.g., from about −5 to about −10 psi, at the face region of each suction cup 408a–408d. Suction picker assembly 394 is then driven up, thereby lifting a heat-sealable cover 342a from stack 342. Picker arm 390 is then rotated another 90°, from the pick-up position to a drop-off position (FIGS. 21 and 22). Here, suction picker assembly 394 is driven down until sheet 342a rests on a multi-well tray 324, at which point the vacuum is released. Suction picker assembly 394 is then raised back up, while suction picker arm 390 is returned to the home position. Next, carriage 376 is moved forward to position platen 412 directly above multi-well tray 324. The TECAN® RSP 198 (FIG. 16) is moved along the x/y direction to position its four fingers 1–4 above respective landing sites 425–429 on top of support plate 414. The TECAN® RSP then presses down, along the z direction, with each of fingers 1–4, thereby compressing the bottom surface of platen 412, heated to about 105°–120° C., against the heat-sealable sheet 342a resting on multi-well tray 324. Heated platen 412 is held against the multi-well tray for a short period (e.g., about 10–20 seconds), at a pressure of about 20 lbs., thereby sealing the heat-sealable sheet 342a onto tray 324. The fingers 14 of the TECAN® RSP 198 are then raised, thereby allowing the heated platen 412 to raise. The above process is repeated for any other multi-well plates held in a cavity 310 of work surface 302.

As previously mentioned, a computer control unit can be programmed, using known techniques, to automate the above process. To this end, non-contact sensors, for example infrared emitter/detector pairs (not shown), and sensor flags, such as flag 476, can be strategically positioned to provide position signals for monitoring by the computer control unit.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed is:

1. An apparatus for avoiding cross-contamination due to pendent drops of fluid hanging from a plurality of discharge conduits disposed in an array above a corresponding array of receiving wells, comprising:
   (i) a carriage configured to carry said discharge-conduit array and adapted for linear reciprocal motion in either of two directions along a first, generally horizontal, axis from a neutral position whereat said arrays are substantially axially aligned; and
   (ii) a vertical positioning assembly supporting said discharge-conduit array for linear movement along a second, generally vertical, axis between (a) a lowered position whereat said discharge conduits extend down into respective receiving wells, (b) an elevated position whereat said discharge conduits clear said receiving wells, and (c) a touch-off position intermediate of said lowered and elevated positions where pendent drops hanging from said discharge conduits contact respective sidewalls of respective ones of said receiving wells upon said linear reciprocal motion.

2. The apparatus of claim 55, further comprising a vacuum chamber communicating with said discharge-conduit array from a side thereof opposite said receiving-well array, whereby evacuation of said vacuum chamber is effective to urge pendent drops of fluid hanging from said discharge conduits in a direction away from said receiving wells and into said discharge conduits.

3. A method for avoiding cross-contamination due to pendent drops of fluid hanging from a plurality of discharge conduits disposed in an array above a corresponding array of receiving wells, comprising:

touching-off, in a substantially simultaneous fashion, said pendent drops of fluid hanging from said discharge conduits to inner sidewalls of respective receiving wells;

wherein said step of touching-off is effected by shifting the discharge-conduit array along a plane substantially orthogonal to the longitudinal axes of the receiving wells, while the receiving wells are maintained in a substantially fixed position; and further wherein each of said discharge conduits is shifted into contact with one sidewall portion of a respective well, and then is shifted into contact with another, laterally opposing sidewell portion of the same receiving well.

4. The method of claim 3, further comprising drawing adherent drops of fluid hanging from said discharge conduits in a direction away from said respective receiving wells and up into said discharge conduits.

* * * * *

UNITED STATES PATENT AND TRADEMARK OFFICE
CERTIFICATE OF CORRECTION

PATENT NO. : 6,783,732 B2
DATED : August 31, 2004
INVENTOR(S) : Alfred P. Madden et al.

It is certified that error appears in the above-identified patent and that said Letters Patent is hereby corrected as shown below:

Column 36,
Line 59, replace "claim 55" with -- claim 1 --.

Column 38,
Line 2, add -- receiving -- following "respective";
Line 4, replace "sidewell" with -- sidewall --.

Signed and Sealed this

Eleventh Day of January, 2005

JON W. DUDAS
*Director of the United States Patent and Trademark Office*